(12) United States Patent      (10) Patent No.: US 11,471,049 B2
Yukimori et al.      (45) Date of Patent: Oct. 18, 2022

(54) OPHTHALMOLOGIC APPARATUS

(71) Applicant: TOPCON CORPORATION, Tokyo (JP)

(72) Inventors: Takafumi Yukimori, Tokyo (JP); Shigeru Okikawa, Tokyo (JP)

(73) Assignee: TOPCON CORPORATION, Tokyo (JP)

(*) Notice: Subject to any disclaimer, the term of this patent is extended or adjusted under 35 U.S.C. 154(b) by 408 days.

(21) Appl. No.: 16/773,088

(22) Filed: Jan. 27, 2020

(65) Prior Publication Data

US 2020/0253472 A1    Aug. 13, 2020

(30) Foreign Application Priority Data

Feb. 7, 2019    (JP) .............................. JP2019-021004

(51) Int. Cl.
    *A61B 3/15*      (2006.01)
    *G06T 7/00*      (2017.01)
    *G06T 19/20*      (2011.01)

(52) U.S. Cl.
    CPC ............ *A61B 3/152* (2013.01); *G06T 7/0012* (2013.01); *G06T 19/20* (2013.01); *G06T 2207/20* (2013.01); *G06T 2207/30041* (2013.01); *G06T 2219/2004* (2013.01)

(58) Field of Classification Search
None
See application file for complete search history.

(56) References Cited

U.S. PATENT DOCUMENTS

| | | | |
|---|---|---|---|
| 2012/0200824 A1* | 8/2012 | Satake | .................... G06T 5/005 351/206 |
| 2012/0242955 A1* | 9/2012 | Yoshino | ............... A61B 3/0091 351/208 |
| 2015/0109578 A1* | 4/2015 | Baranton | ............. A61B 3/0075 351/205 |
| 2016/0091720 A1 | 3/2016 | Stafford et al. | |

FOREIGN PATENT DOCUMENTS

JP      2018-89079      6/2018

OTHER PUBLICATIONS

Extended European Search Report dated Jul. 1, 2020 in corresponding European Patent Application No. 20155606.5.

* cited by examiner

*Primary Examiner* — Frank S Chen
(74) *Attorney, Agent, or Firm* — Wenderoth, Lind & Ponack, L.L.P.

(57) ABSTRACT

An ophthalmologic apparatus comprises eye information obtaining portions, each of the eye information obtaining portions corresponding to each of subject eyes of a subject and configured to obtain information on each of the subject eyes; imaging portions, each of the imaging portions corresponding to each of the eye information obtaining portions and configured to capture a subject eye image of each of the subject eyes; a reference calculator configured to obtain a three-dimensional reference position in each of the subject eye images captured by each of the imaging portions; an inclination calculator configured to obtain inclination information indicating inclination of relative positions of the subject eyes from the obtained three-dimensional reference positions in the subject eye images; and a notification portion configured to notify the obtained inclination information.

4 Claims, 9 Drawing Sheets

OPHTHALMOLOGIC APPARATUS

CROSS-REFERENCE TO RELATED APPLICATION

The present application is based on and claims priority from Japanese Patent Application No. 2019-21004 filed on Feb. 7, 2019, the disclosure of which is hereby incorporated by reference in its entirety.

FIELD OF THE INVENTION

The present disclosure relates to an ophthalmologic apparatus.

BACKGROUND

An ophthalmologic apparatus is known in the art to obtain information on subject eyes such as the characteristics of the subject eyes by eye information obtaining portions. The ophthalmologic apparatus may obtain incorrect information on the subject eyes when the subject eyes incline upon obtaining the information.

Accordingly, the conventional ophthalmologic apparatus obtains the inclinations of the subject eyes and corrects the inclinations in the obtained information by a correction portion (see Patent Literature 1: JP2018-89079A, for example). The ophthalmologic apparatus corrects the obtained information on the subject eyes to a state where the inclinations of the subject eyes have been canceled.

In general, when an examinee or subject inclines his or her head or face, a physiological phenomenon called counter-rotation of the eyeballs occurs. The counter-rotation of the eyeballs rotates the eyeballs to cancel the inclinations of the eyeballs. The extraocular muscles are used when canceling the inclinations of the eyeballs. Accordingly, the eyeballs (i.e. the subject eyes) may be measured while in a state different from the natural state of the eyes. Consequently, in the conventional ophthalmologic apparatus, the corrected information on the subject eyes after canceling the inclinations may differ from the information on the subject eyes in the natural state.

The present disclosure is made by considering the above issue, and an object of the present disclosure is to provide an ophthalmologic apparatus that facilitates obtaining information on the subject eyes in the natural state.

SUMMARY

To solve the above issue, the ophthalmologic apparatus of the present disclosure includes eye information obtaining portions, each of the eye information obtaining portions corresponding to each of subject eyes of a subject and configured to obtain information on each of the subject eyes; imaging portions, each of the imaging portions corresponding to each of the eye information obtaining portions and configured to capture a subject eye image of each of the subject eyes; a reference calculator configured to obtain a three-dimensional reference position in each of the subject eye images captured by each of the imaging portions; an inclination calculator configured to obtain inclination information indicating inclination of relative positions of the subject eyes from the obtained three-dimensional reference positions in the subject eye images; and a notification portion configured to notify the obtained inclination information.

DETAILED DESCRIPTION

Hereinafter, an ophthalmologic apparatus 10 according to an embodiment of the present disclosure will be described with reference to FIGS. 1 to 10. It should be noted that deflection members 26 are not shown in FIGS. 5 and 6 to facilitate the understanding of components and structures shown in the figures.

The ophthalmologic apparatus 10 according to the present disclosure includes eye information obtaining portions configured to obtain information on the subject eyes. As the obtaining of the information on the subject eyes, the ophthalmologic apparatus performs at least one of capturing images (taking pictures) of the subject eyes (e.g. an anterior eye part, a fundus, etc.) and obtaining the characteristics of the subject eyes. As the obtaining of the characteristics of the subject eyes, the ophthalmologic apparatus of the present disclosure performs at least one of a subjective examination and an objective examination. In the subjective examination, a visual target or the like is presented to a subject and test results are obtained based on the response of the subject to the visual target or the like. The subjective examination includes examinations and measurements such as a subjective refraction measurement, a glare examination, a distance examination, a near distance examination, a contrast inspection, and a visual field examination. In the objective examination, the characteristics of the subject eyes are measured by projecting the light to the subject eyes and receiving the returned light. The information on the subject eyes is obtained based on the detection result of the returned light. The objective examination includes a measurement for obtaining the characteristics of the subject eyes and a photographing for obtaining the subject eye images. In addition, the objective examination includes measurements such as an objective refraction measurement (ref measurement), a corneal shape measurement (kerato measurement), an intraocular pressure measurement, fundus photography, tomography by using optical coherence tomography (referred to as "OCT" hereinafter) (OCT photography), and a measurement by using OCT.

The ophthalmologic apparatus 10 in this embodiment is an ophthalmologic apparatus that simultaneously measures the characteristics of both eyes (i.e. subject eyes E) while the subject keeps both eyes open. Also, the ophthalmologic apparatus 10 separately measures each of the eyes by blocking one of the eyes or turning off the fixed visual target, for example.

Figure 1:
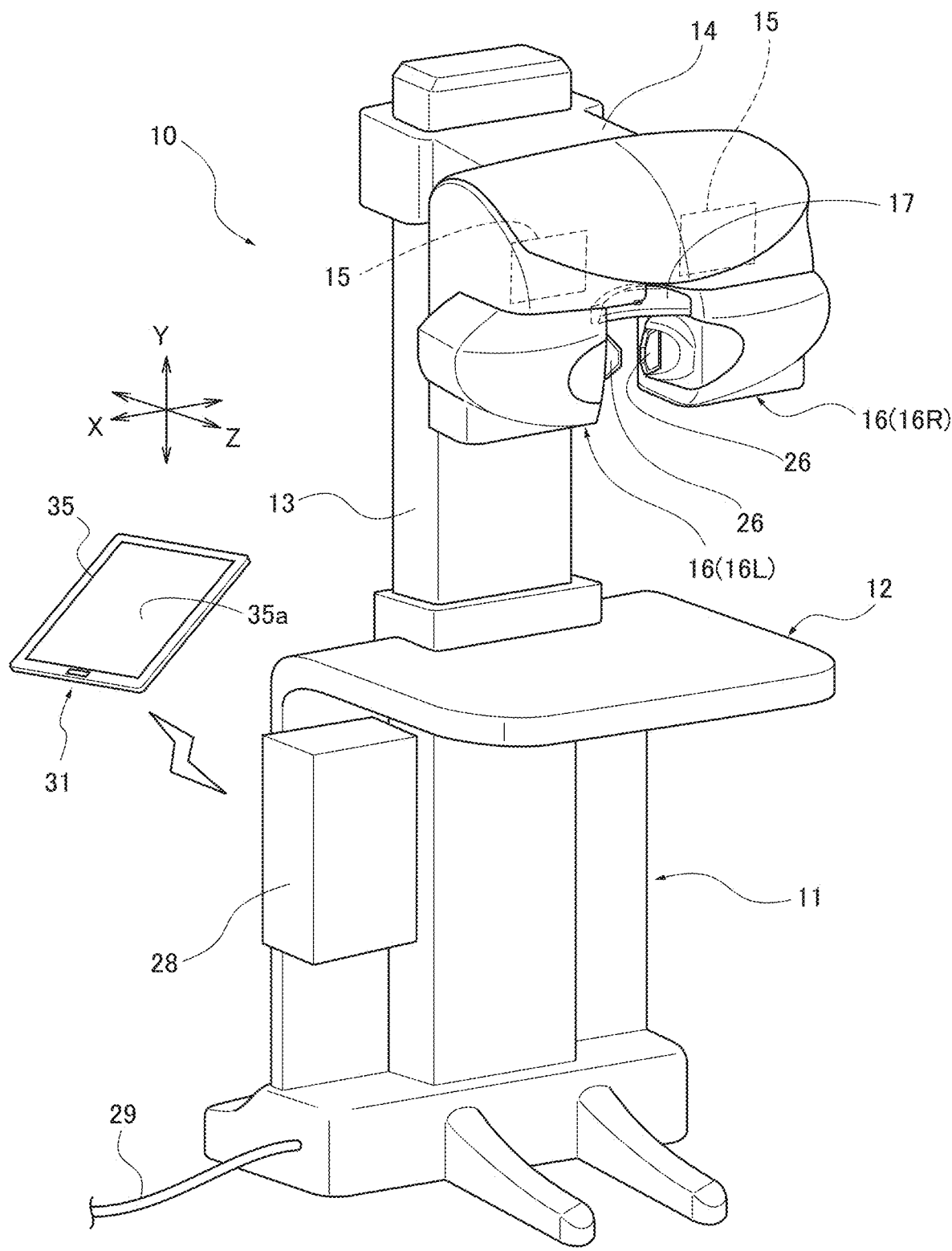
FIG. 1 is a perspective view illustrating the entire structure of an ophthalmologic apparatus according to an embodiment of the present disclosure.

As shown in FIG. 1, the ophthalmologic apparatus 10 includes a base 11 placed on a floor, an optometry table 12, an upright member 13, a supporting arm 14, a drive mechanism 15, and a pair of measurement heads 16. A forehead holder 17 is disposed between the measurement heads 16. The ophthalmologic apparatus 10 is configured to obtain information on the subject eyes E (see FIG. 3, etc.) of the subject when the subject is in front of the optometry table 12 and puts his or her forehead on the forehead holder 17. Hereinafter, a left and right direction of the ophthalmologic apparatus 10 is referred to as an X direction; an up and down direction (i.e. vertical direction) of the apparatus 10 is referred to as a Y direction, and a front and rear direction of the apparatus 10 is referred to as a Z direction. The Z direction is perpendicular to the X and Y directions. In the Z direction, a side where the subject is located during the measurement is referred to as a front side (or a front direction).

The optometry table 12 is supported by the base 11. On the optometry table 12, a controller for the examiner (referred to as the examiner controller 31), a controller for the subject (referred to as the subject controller 32), items used during the measurement or examination, and the like are placed. The optometry table 12 may be adjustable in the Y direction (height position).

The upright member 13 is supported by the base 11 and extends along the rear edge of the optometry table 12 in the Y direction. The arm 14 is attached to the upper end of the upright member 13 and extends in the Z direction from the upright member 13 to the front side. The arm 14 supports the pair of measurement heads 16 via the drive mechanism 15 above the optometry table 12. In other words, the measurement heads 16 are suspended and supported by the drive mechanism 15 at the front end of the arm 14. The arm 14 is movable in the Y direction along the upright member 13 and the position of the arm 14 is adjustable in the Y direction by an arm drive mechanism 34, which will be described later with reference to FIG. 4. It should be noted that the arm 14 may be movable in the X and Z directions relative to the upright member 13.

The pair of measurement heads 16 correspond to the right and left subject eyes E of the subject, respectively. Hereinafter, the measurement head for the left eye is referred to as a left measurement head 16L and the measurement head for the right eye is referred to as a right measurement head 16R. The left measurement head 16L is configured to obtain information on the left subject eye E of the subject, and the right measurement head 16R is configured to obtain information on the right subject eye of the subject. The left measurement head 16L and the right measurement head 16R are arranged symmetrically with respect to a vertical plane in the middle of the measurement heads 16L, 16R in the X direction. In other words, the configurations of the left and right measurement heads 16L, 16R are symmetrical relative to the vertical plane.

Figure 2:
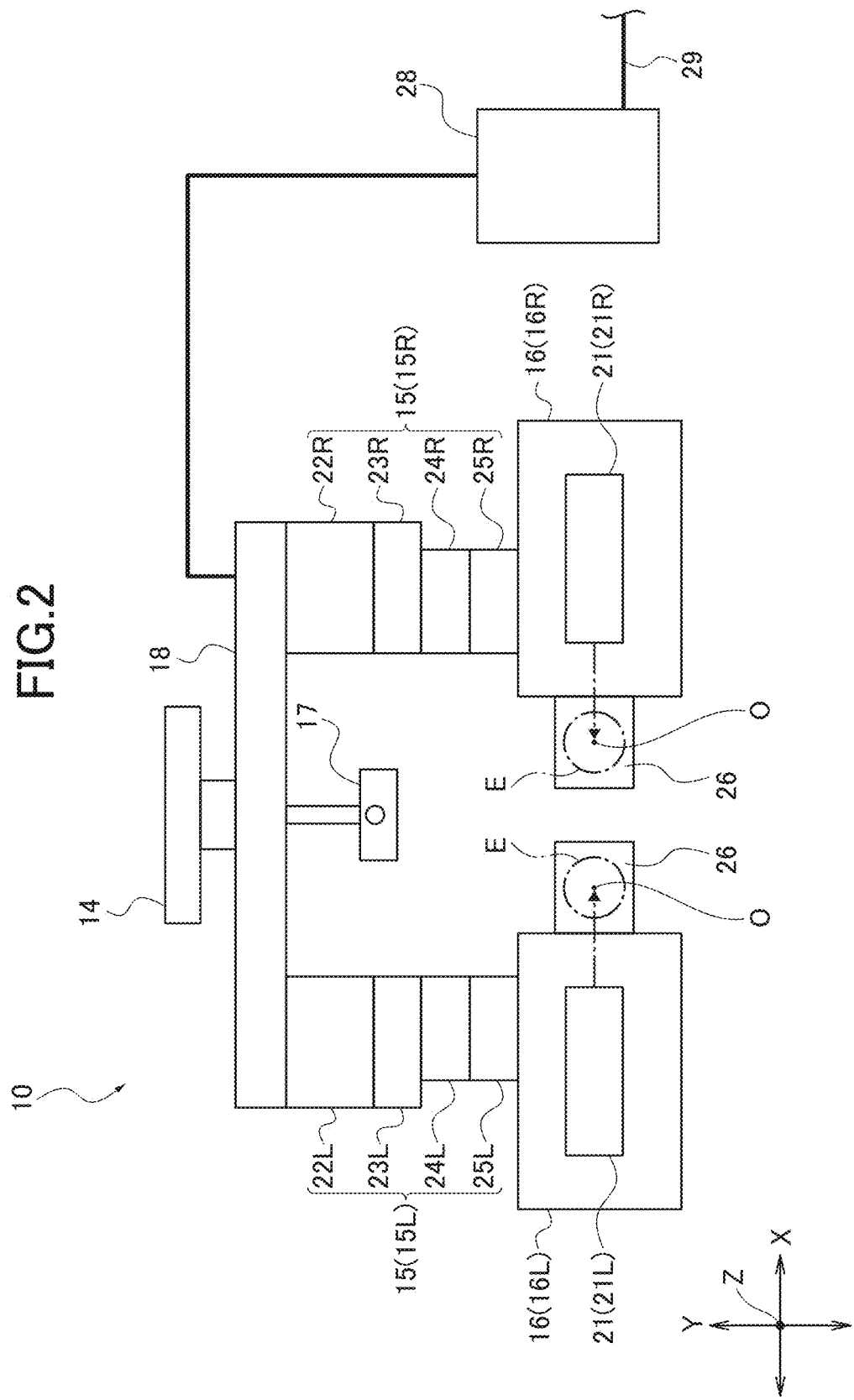
FIG. 2 is a schematic view illustrating a pair of measurement heads that are movable via a drive mechanism in the ophthalmologic apparatus.

Each of the measurement heads 16 includes an eye information obtaining portion 21 configured to obtain information on a respective subject eye E. Specifically, the left measurement head 16L includes a left eye information obtaining portion 21L, and the right measurement head 16R includes a right eye information obtaining portion 21R as shown in FIG. 2. The information on the subject eyes E (also referred to as eye information) may be the combination of the refractive power of the subject eyes E, the images of the subject eyes E (e.g. the anterior eye part images I, see FIG. 5), the images of the fundi Ef of the subject eyes E (see FIG. 5), the tomographic images of the retinae of the subject eyes E, the images of the corneal endothelium of the subject eyes E, the cornea shape of the subject eyes E, the intraocular pressure of the subject eyes E, or the like. Each of the eye information obtaining portions 21 is configured by suitably combining at least some of a refractive power measurement mechanism, a visual target provider, a visual acuity test device, a phoropter, a wavefront sensor, a fundus camera, an optical coherence tomography (OCT), a specular microscope, a keratometer, a tonometer, and the like. The refractive power measurement mechanism (refractometer in this embodiment) is configured to measure the refractive power. The visual target provider is configured to provide the visual target on the optical axis. The visual acuity test device is configured to test the visual acuity of the subject while switching the visual targets. The phoropter is configured to obtain the corrective refractive power of the subject eyes E by switching the corrective lenses. The wavefront sensor is configured to measure the refractive power. The fundus camera is configured to capture the images of the fundus. The optical coherence tomography (OCT) is configured to capture the tomographic images of the retina. The specular microscope is configured to capture the images of the corneal endothelium. The keratometer is configured to measure the shape of the corneal. The tonometer is configured to measure the intraocular pressure.

As shown in FIG. 2, the measurement heads 16 are movably supported by the drive mechanism 15 via an attachment base 18. The attachment base 18 is fixed to the front end of the arm 14 to extend in the X direction. The left drive mechanism 15L is suspended from one end of the attachment base 18 and the right drive mechanism 15R is suspended from the other end of the attachment base 18. The forehead holder 17 is disposed in the center of the attachment base 18.

In this embodiment, the drive mechanism 15 includes a drive mechanism 15L for the left eye and a drive mechanism 15R for the right eye. Hereinafter, the drive mechanism 15L for the left eye is referred to as a left drive mechanism 15L and the drive mechanism 15R for the right eye is referred to as a right drive mechanism 15R. The left drive mechanism 15L corresponds to the left measurement head 16L and the right drive mechanism 15R corresponds to the right measurement head 16R. The left drive mechanism 15L includes a left vertical drive portion 22L, a left horizontal drive portion 23L, a left Y-axis rotary drive portion 24L, and a left X-axis rotary drive portion 25L. The right drive mechanism 15R includes a right vertical drive portion 22R, a right horizontal drive portion 23R, a right Y-axis rotary drive portion 24R, and a right X-axis rotary drive portion 25R. The left drive mechanism 15L and the right drive mechanism 15R are arranged symmetrically with respect to a vertical plane in the middle of drive mechanisms 15L, 15R in the X direction. In other words, the configurations of the left and right drive mechanisms 15L, 15R and the drive portions thereof are symmetrical relative to the vertical plane. Accordingly, the vertical drive portion 22, the horizontal drive portion 23, the Y-axis rotary drive portion 24, and X-axis rotary drive portion 25 are used to explain them when it is unnecessary to distinguish the right drive portions 22R, 23R, 24R, 25R and the left drive portions 22L, 23L, 24L, 25L. In the drive mechanism 15, the vertical drive portion 22, the horizontal drive portion 23, the Y-axis rotary drive portion 24, and the X-axis rotary drive portion 25 are arranged from the attachment base 18 to the measurement heads 16 in this order.

The vertical drive portion 22 is disposed between the attachment base 18 and the horizontal drive portion 23 and configured to move the horizontal drive portion 23 relative to the attachment base 18 in the Y direction (i.e. the vertical direction). The horizontal drive portion 23 is disposed between the vertical drive portion 22 and the Y-axis rotary drive portion 24 and configured to move the Y-axis rotary drive portion 24 relative to the vertical drive portion 22 in the X and Z directions (i.e. the horizontal direction). The vertical drive portion 22 and the horizontal drive portion 23 are respectively configured to include an actuator that generates a driving force and a transmission mechanism that transmits the driving force. For example, the actuator may be a pulse motor or the like and the transmission mechanism may include gears, a rack and pinion or the like. For example, the horizontal drive portion 23 can be easily configured by including the actuator and the transmission mechanism for the X and Y directions, respectively and can facilitate the control of the movement in the X and Y directions.

The Y-axis rotary drive portion 24 is disposed between the horizontal drive portion 23 and the X-axis rotary drive portion 25. The Y-axis rotary drive portion 24 is configured to rotate the X-axis rotary drive portion 25 relative to the horizontal drive portion 23 about an eyeball rotation Y-axis. The eyeball rotation Y-axis extends in the Y direction through an eyeball rotation point O of the corresponding subject eye E. The X-axis rotary drive portion 25 is disposed between the Y-axis rotary drive portion 24 and the corresponding measurement head 16. The X-axis rotary drive portion 25 is configured to rotate the corresponding measurement head 16 relative to the Y-axis rotary drive portion 24 about an eyeball rotation X-axis. The eyeball rotation X-axis extends in the X direction through the eyeball rotation point O of the corresponding subject eye E.

Similar to the vertical drive portion 22 and the horizontal drive portion 23, the Y-axis rotary drive portion 24 and the X-axis rotary drive portion 25 include an actuator and a transmission mechanism, respectively. The transmission mechanisms of the Y-axis rotary drive portion 24 and the X-axis rotary drive portion 25 are configured to move along respective circular guide grooves by the driving force from the actuator. The Y-axis rotary drive portion 24 is configured to rotate the measurement head 16 about the eyeball rotation Y-axis of the subject eye E when the center of the circular guide groove is coincident with the eyeball rotation Y-axis. Similarly, the X-axis rotary drive portion 25 is configured to rotate the measurement head 16 about the eyeball rotation X-axis of the subject eye E when the center of the circular guide groove is coincident with the eyeball rotation X-axis. In other words, the measurement head 16 is configured to rotate about the eyeball rotation point O in a rotation direction about the Y direction and a rotation direction about the X direction when the centers of the circular guide grooves of the Y-axis rotary drive portion 24 and the X-axis rotary drive portion 25 are coincident with the eyeball rotation point O of the subject eye, respectively.

The Y-axis rotary drive portion 24 may support the measurement head 16 movable about a rotation Y-axis of the Y-axis rotary drive portion 24 and rotate the measurement head 16 about the eyeball rotation Y-axis of the subject eye E by changing and rotating the supporting position of the measurement head 16 in cooperation with the horizontal drive portion 23 via the X-axis rotary drive portion 25. Also, the X-axis rotary drive portion 25 may support the measurement head 16 movable about a rotation X-axis of the X-axis rotary drive portion 25 and rotate the measurement head 16 about the eyeball rotation X-axis of the subject eye E by changing and rotating the supporting position of the measurement head 16 in cooperation with the vertical drive portion 22.

According to the above configuration, the drive mechanisms 15L, 15R can move the measurement heads 16 separately or collectively in the X direction, the Y direction, and the Z direction, and rotate the measurement heads 16 about the eyeball rotation points O of the corresponding subject eyes E in the rotation direction about the Y direction and the rotation direction about the X direction. In addition, the drive mechanisms 15L, 15R can move the measurement heads 16 to the positions corresponding to the rotations of the subject eyes E, respectively. Further, each of the drive mechanisms 15L, 15R adjusts the position of each measurement head 16 so that the corresponding subject eye E can be diverged (diverting movement) or converged (converging movement). Thereby, the ophthalmologic apparatus 10 can measure the various characteristics of the subject eyes E by carrying out examinations on the diverting movement and the converging movement, a distance examination and a near distance examination in the binocular vision state of the subject eyes E.

Figure 3:
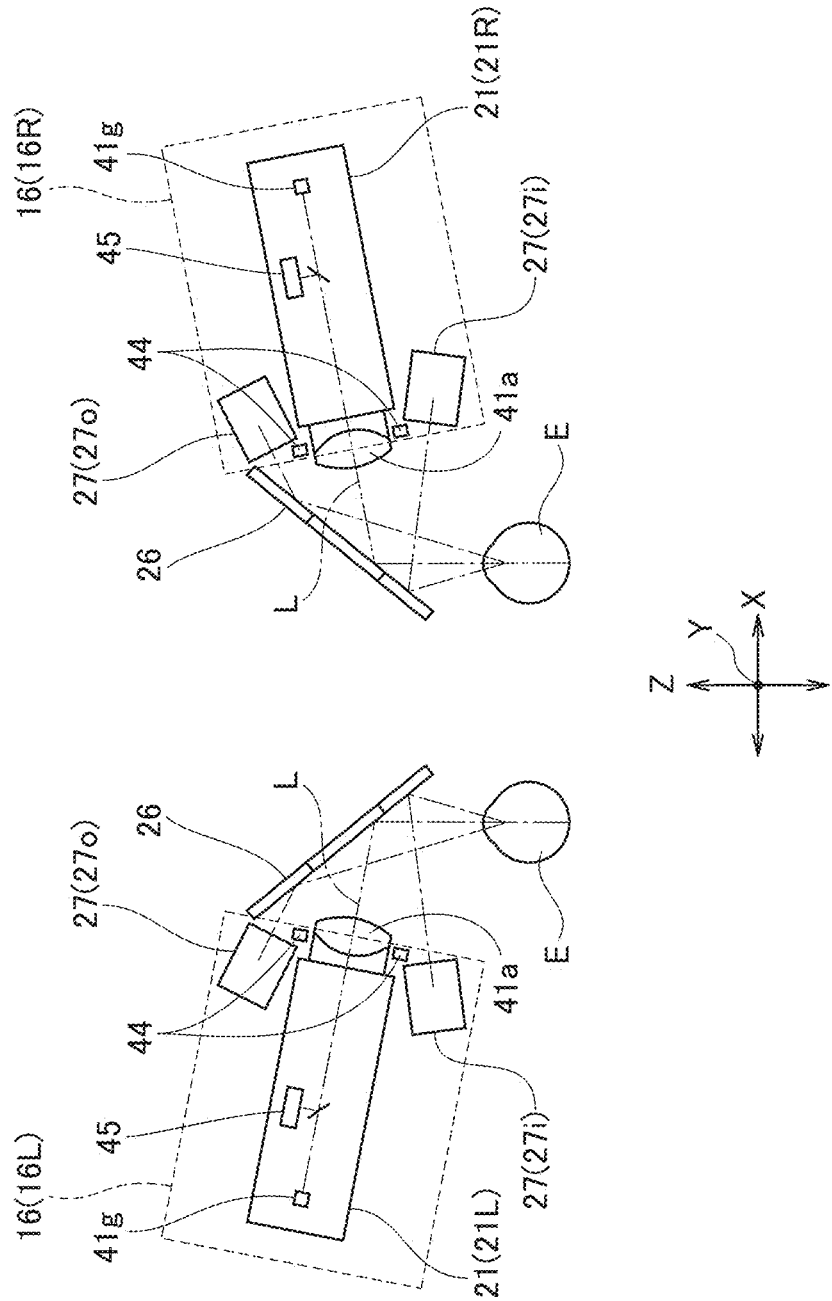
FIG. 3 is a schematic view illustrating eye information obtaining portions of the ophthalmologic apparatus.

Each of the measurement heads 16 includes a deflection member 26. The eye information obtaining portion 21 of the measurement head 16 can obtain the information on the corresponding subject eye E via the deflection member 26. As shown in FIG. 3, the ophthalmologic apparatus 10 adjusts the positions of the measurement heads 16 such that the deflection members 26 are set to respective positions corresponding to the left and right subject eyes E, so that the information on the subject eyes E can be simultaneously obtained with the subject eyes diverged (in the binocular vision state). In addition, the X-axis rotary drive portions 25L, 25R change the rotation positions of the measurement heads 16 about the eyeball rotation X-axis, and accordingly the ophthalmologic apparatus 10 can obtain the information on the subject eyes E while the subject is looking downward or upward with the subject eyes E. Further, the Y-axis rotary drive portions 24L, 24R change the rotation positions of the measurement heads 16 about the eyeball rotation Y-axis, and accordingly the ophthalmologic apparatus 10 can obtain the information on the subject eyes E while the subject is looking left or right with the subject eyes E.

The ophthalmologic apparatus 10 includes a pair of imaging portions each corresponding to a respective one of the subject eyes E. Each of the imaging portions comprises two or more imaging devices (cameras 27 in this embodiment) each configured to capture an image of the respective one of the subject eyes from a direction different from others. In one embodiment, each of the measurement heads 16 includes a plurality of cameras 27 which are disposed in the vicinity of the deflection member 26. The cameras 27 are configured to capture the images of one of the subject eyes E corresponding to the measurement head 16. In this embodiment, each of the measurement heads 16 includes two cameras 27 which constitute a stereo camera. In other words, the ophthalmologic apparatus 10 includes four cameras 27 in total. The two cameras 27 are respectively disposed in the front and rear sides of the eye information obtaining portion 21 in the Z direction with an optical axis L of the eye information obtaining portion 21 therebetween.

The two cameras 27 are provided for each of the subject eyes E and each of the cameras 27 captures the images of the corresponding subject eye E from a direction different from the other camera 27. In another embodiment, the imaging portion includes two or more cameras 27 (i.e. imaging devices). The light from the corresponding subject eye E enters the cameras 27 after deflected by the deflection member 26, and thereby, each of the cameras 27 captures the subject eye image Ie (see FIG. 6, etc.). The subject eye images Ie captured by the cameras 27 are images of the corresponding subject eye E obliquely viewed from different directions which are inclined relative to an optical axis L of an observation system 41. The two cameras 27 are arranged in the Z direction, and one of the cameras 27 is positions forward of the other camera 27 in the Z direction relative to the corresponding subject eye E. The deflection member 26 allows the cameras 27 to obtain the subject eye images Ie of the corresponding subject eye E from positions inclined relative to the X direction. Accordingly, one of the cameras 27 constitutes an outer camera 27o which obtains the subject eye image Ie from the outside of the subject, and the other of the cameras 27 constitutes an inner camera 27i which obtains the subject eye image Ie from the inside of the subject. In this case, the inside of the subject means a nose side of the subject, and the outside of the subject means the opposite side of the nose side.

The two cameras 27 may be arranged substantially in the Y direction (i.e. vertical direction) relative to the corresponding subject eye E. However, in the subject eye images Ie captured obliquely from the Y direction, an area of the corresponding subject eye E covered by the eyelid increases when the eyelid of the corresponding subject eye E is slightly closed. Accordingly, it is preferable that the cameras 27 are arranged to obtain the subject eye images Ie substantially from the X direction since this arrangement is less affected even when the eyelid of the corresponding subject eye E is slightly closed. In addition, it is preferable that the two of the cameras 27 are arranged to obtain the subject eye images Ie obliquely from below the subject eye E in the X direction since the eyelids of the older subject tend to be lowered.

The two cameras 27 obtain two different subject eye images Ie at the same time by substantially simultaneously photographing the corresponding subject eye E. Here, the term "substantially simultaneously" means that the difference between the photographing timing of the two cameras 27 is so small that movement of the eye can be ignored when the two cameras 27 are capturing images. The two cameras 27 simultaneously photograph the corresponding subject eye E from the different directions to obtain two or more subject eye images Ie. In other words, the position (or direction) of the subject eye E when photographing with one of the cameras 27 is the same as the position (or direction) of the subject eye E when photographing with the other of the cameras 27. Thereby, the two cameras 27 can be used to obtain the three-dimensional position of the corresponding subject eye E, which will be described later.

In this embodiment, the two cameras 27 (imaging devices) are provided for each of the subject eyes E. However, the number of the cameras 27 is not limited to two but more than two cameras may be provided for each of the subject eyes E. Considering the calculation process for obtaining the three-dimensional position, which will be described later, the configuration that can substantially simultaneously capture the images of the corresponding subject eye (e.g. its anterior eye part) from the two different directions is sufficient. In this embodiment, the two cameras 27 are provided separately from the eye information obtaining portion 21 (its observation system 41) for each of the subject eyes E. However, the arrangement of the cameras 27 is not limited to this embodiment, and one of the cameras 27 may be replaced with the observation system 41 if the corresponding subject eye E can be substantially simultaneously photographed from the two or more different directions. In this embodiment, each of the imaging portions includes the two cameras but is not limited to this embodiment. Each of the imaging portions may include the observation system 41 or may have any configuration if it can obtain the images of each subject eye E.

Figure 4:
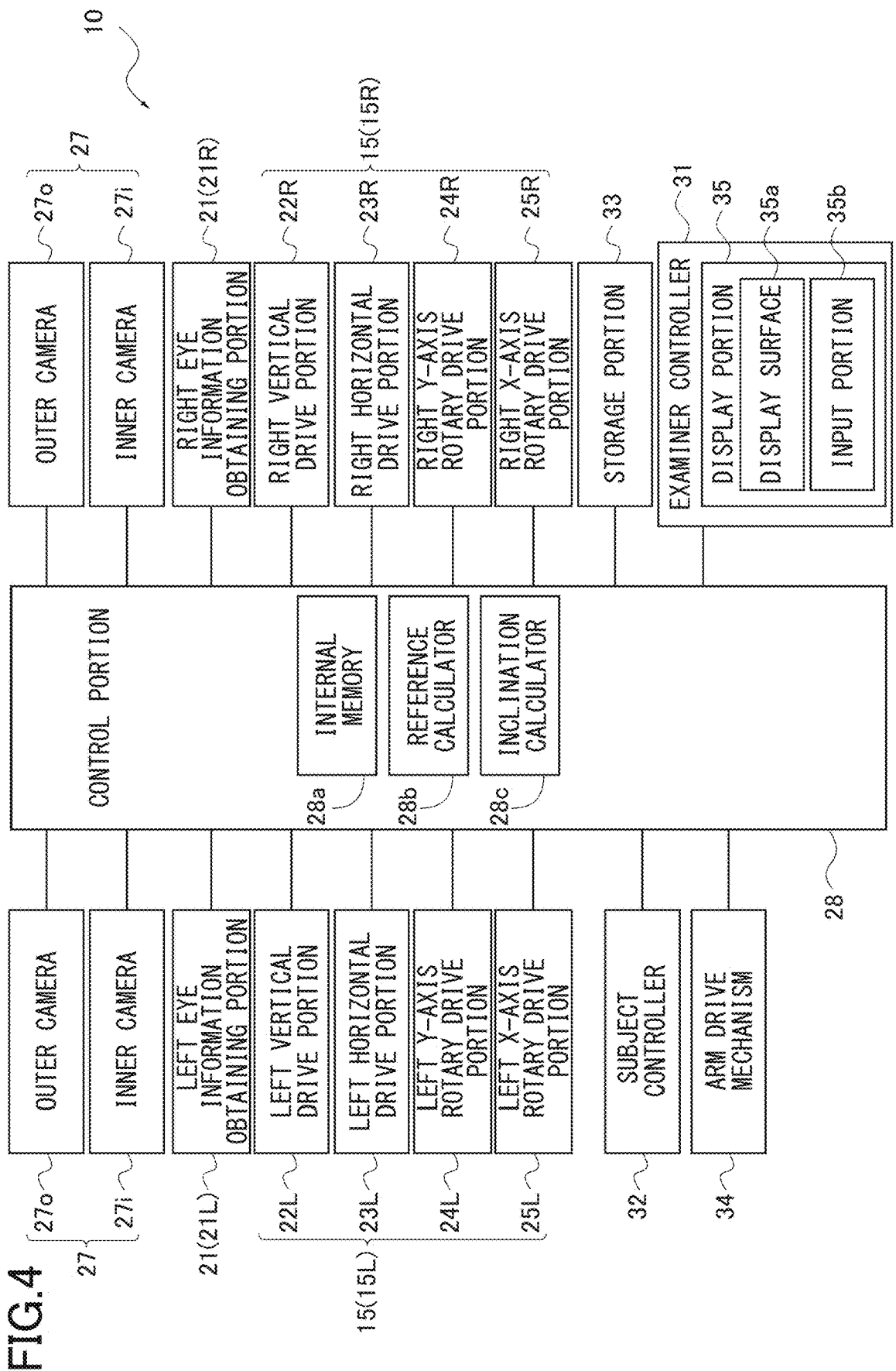
FIG. 4 is a block diagram illustrating a control system of the ophthalmologic apparatus.

As shown in FIG. 1, a control portion 28 is disposed within a control box which is fixed to the base 11. The control portion 28 is configured to centrally control the portions of the ophthalmologic apparatus 10. As shown in FIG. 4, the eye information obtaining portions 21, the vertical drive portions 22, the horizontal drive portions 23, the Y-axis rotary drive portions 24, and the X-axis rotary drive portions 25 as the drive mechanisms 15, the cameras 27 (the outer cameras 27o, and the inner cameras 27i), the examiner controller 31, the subject controller 32, the storage portion 33, and the arm drive mechanism 34 are connected to the control portion 28. In the ophthalmologic apparatus 10, a commercial power supply supplies electric power to the control portion 28 via a cable 29 (see FIGS. 1 and 2) and the control portion 28 supplies the electric power to the drive mechanisms 15 and the measurement heads 16 (i.e. the eye information obtaining portions). The control portion 28 can control the operations of the drive mechanisms 15 and the measurement heads 16 (i.e. the eye information obtaining portions 21) and exchange information with them.

The examiner controller 31 is used by the examiner to operate the ophthalmologic apparatus 10. The examiner controller 31 is connected to the control portion 28 to communicate with each other by short-range wireless communication. The examiner controller 31 only needs to be connected to the control portion 28 via a wired or wireless communication path and is not limited to the configuration of this embodiment. As the examiner controller 31 of this embodiment, a portable terminal (information processing apparatus) such as a tablet terminal or a smartphone is used. Note that the examiner controller 31 is not limited to the portable terminal but may be a laptop computer, a desktop computer, or the like. Also, the examiner controller 31 may be fixed or attached to the ophthalmologic apparatus 10.

The examiner controller 31 includes a display 35 which is a liquid crystal monitor in this embodiment. The display 35 includes a display surface 35a (see FIG. 1, etc.) on which images or the like are displayed, and an input portion 35b superimposed on the display surface 35a. The input portion 35b is touch panel-type in this embodiment. The examiner controller 31 is configured to display anterior eye part images I (see FIG. 5) based on the image signals from image sensors 41g in the observation systems 41, the subject eye images Ie (see FIG. 6, etc.) from the cameras 27, measurement ring images Ri (see FIG. 10), the fundus images, and the like on the display surface 35a under control of the control portion 28. In addition, the examiner controller 31 is configured to display the input portion 35b on the display surface 35a under control of the control portion 28 and to output operation information such as input alignment instructions and measurement instructions to the control portion 28.

The subject controller 32 is used by the subject in response to the examination or inspection such that various information on the subject eyes E is obtained. The subject controller 32 is connected to the control portion 28 via a wired or wireless communication path. The subject controller 32 is a keyboard, a mouse, a joystick, or the like, for example.

The control portion 28 extracts a program stored in the storage portion 33 connected thereto or in a built-in internal memory 28a on a RAM (Random Access Memory) for example and comprehensively controls the operation of the ophthalmologic apparatus 10 in accordance with the operations of the examiner controller 31 and the subject controller 32. In this embodiment, the internal memory 28a is configured by the RAM or the like, and storage portion 33 is configured by a ROM (read-only memory), an EEPROM (electrically erasable programmable ROM), or the like. In addition to the above configurations, the ophthalmologic apparatus 10 may include a printer that prints out measurement results in response to measurement completion signals and instructions from a measurer, and/or an output portion that outputs measurement results to an external memory or a server.

Now, the optical system of the eye information obtaining portions 21 will be described with reference to FIG. 5. As described above, the right eye information obtaining portion 21R and the left eye information obtaining portion 21L have the substantially same structure, and accordingly, the right and right eye information obtaining portions 21R, 21L are described as the eye information obtaining portions 21 without distinguishing them.

Figure 5:
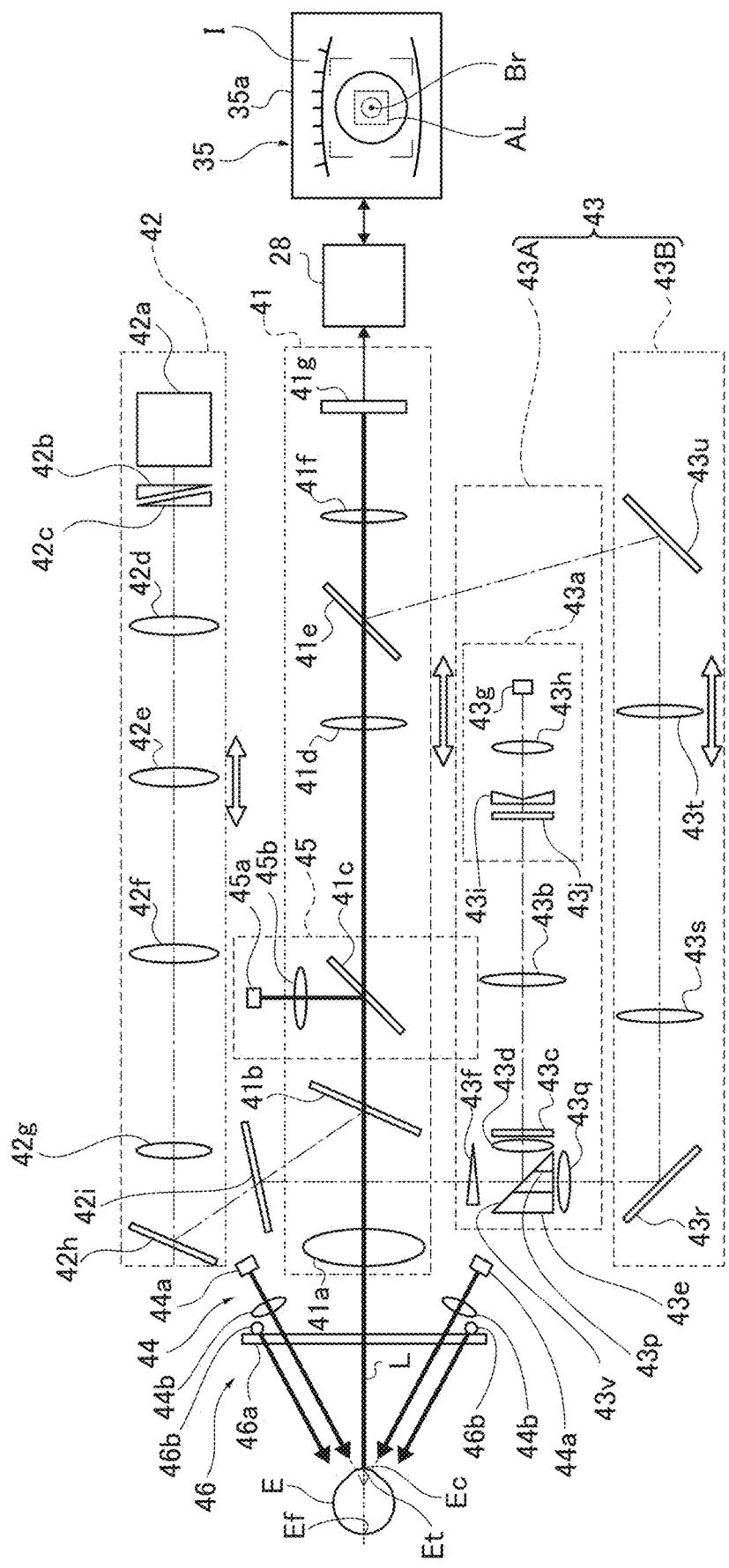
FIG. 5 is an explanatory view illustrating an optical system of the eye information obtaining portion.

As shown in FIG. 5, each of the optical systems of the eye information obtaining portions 21 includes the observation system 41, a visual target projection system 42, an eye refractive power measurement system 43, a Z-alignment system 44, an XY-alignment system 45, and a kerato system 46. The observation system 41 is configured to observe the anterior eye part of the subject eye E. The visual target projection system 42 is configured to provide the visual target to the subject eye E. The eye refractive power measurement system 43 measures the eye refractive power (refraction characteristic) of the subject eye E. The Z-alignment system 44 and the XY-alignment system 45 are configured to align the optical system relative to the subject eye E. The Z-alignment system 44 is configured to generate alignment information in the Z direction (the front and rear direction) along the optical axis L of the observation system 41. The XY-alignment system 45 is configured to generate alignment information in the Y direction (the up and down direction) and the X direction (the left and right direction) which are perpendicular to the optical axis L. The kerato system 46 is configured to measure the shape of the cornea.

The observation system 41 includes an objective lens 41a, a dichroic filter 41b, a half mirror 41c, a relay lens 41d, a dichroic filter 41e, an imaging lens 41f, and an image sensor 41g. The observation system 41 forms an image of the luminous flux or light beams reflected by the subject eye E (the anterior eye part) through the objective lens 41a on the image sensor 41g (its light-receiving surface) by the imaging lens 41f. Thereby, the image sensor 41g is configured to detect (receive) an anterior eye part image I in which a kerato ring luminous flux, luminous flux from an alignment light source 44a, and luminous flux (bright spot image Br) from an alignment light source 45a are projected. The control portion 28 displays the anterior eye part image I and the like on the display surface 35a of the display 35 based on the image signal from the image sensor 41g. The kerato system 46 is provided forward of the objective lens 41a.

The kerato system 46 includes a kerato plate 46a and kerato ring light sources 46b. The kerato plate 46a is disposed in the vicinity of the objective lens 41a. The kerato plate 46a is a plate having at least one concentric (ring-shaped) slit (e.g. one to three slits) with regard to the optical axis L of the observation system 41. The kerato ring light sources 46b are provided to correspond to the slit of the kerato plate 46a. The kerato system 46 projects the kerato ring luminous flux (ring-shaped visual target for corneal curvature measurement) for measuring the shape of the cornea onto the subject eye E (its cornea Ec). The kerato ring luminous flux is formed by the luminous flux (light beams) from the kerato ring light sources 46b flowing through the slit of the kerato plate 46a. The kerato ring luminous flux is reflected by the cornea Ec of the subject eye E and the observation system 41 forms an image on the image sensor 41g. Then, the image sensor 41g detects the image of the ring-shaped kerato ring luminous flux. The control portion 28 displays the image of the measurement pattern on the display surface 35a based on the image signal from the image sensor 41g and executes the kerato measurement to measure the shape of the cornea (curvature radius) by a well-known technique. In this embodiment, as the corneal shape measurement system for measuring the shape of the cornea, the kerato plate 46a (the kerato system 46) which may have one to three ring-shaped slits is used to measure the curvature near the center of the cornea. However, the configuration is not limited to this embodiment, and a placido plate which has multiple rings and is configured to measure the shape of the entire cornea may be used. Alternatively, other configurations may be used. The Z-alignment system 44 is provided rearward of the kerato system 46 (the kerato plate 46a).

The Z-alignment system 44 includes a pair of alignment light sources 44a and a pair of projection lenses 44b. In the Z-alignment system 44, the projection lenses 44b convert the luminous flux from the alignment light sources 44a to parallel luminous flux, and the parallel luminous flux is projected onto the cornea Ec of the subject eye E through an opening in the kerato plate 46a. The parallel luminous flux is detected as alignment information of a bright spot (bright spot image) projected onto the cornea Ec. Thereby, the visual target for the Z direction alignment is projected onto the cornea Ec of the subject eye E. This visual target is detected as a virtual image (Purkinje image) due to corneal surface reflection. The control portion 28 executes the alignment in the Z direction (i.e. the front and rear direction) along the optical axis L of the optical system in the eye information obtaining portion 21 by moving the measurement head 16 in the Z direction via the horizontal drive portion 23 such that that the ratio of a distance between the two bright spot images and the diameter of the kerato ring image is within a predetermined range. The control portion 28 may obtain the amount of deviation of the alignment from the above ratio and display the amount of deviation of the alignment on the display surface 35a. It should be noted that the alignment in the Z direction may be executed by adjusting the position of the right measurement head 16R such that the bright spot image from an alignment light source 45a can be in focus. In addition, the alignment using the visual target in the Z-alignment system 44 may include alignments in the X and Y directions. Further, the alignment in the Z direction may be executed by using two subject eye images Ie from the two cameras 27.

The observation system 41 includes an XY-alignment system 45. The XY-alignment system 45 includes the alignment light source 45a and a projection lens 45b. The XY-alignment system 45 shares the half mirror 41c, the dichroic filter 41b and the objective lens 41a with the observation system 41. In the XY-alignment system 45, luminous flux from the alignment light source 45a is converted to parallel luminous flux through the objective lens 41a and the parallel luminous flux is projected onto the cornea Ec on the optical axis L. The parallel luminous flux draws a virtual image (Purkinje image) because of the corneal surface reflection, and the observation system 41 (its image sensor 41g) detects the bright spot image Br which is the virtual image. The bright spot (the bright spot image Br) is formed at a substantially intermediate location between a corneal vertex Et and the center of curvature of the cornea Ec. The control portion 28 executes the alignments in the X and Y directions (i.e. directions perpendicular to the optical axis L) by driving the vertical drive portion 22 and the horizontal drive portion 23 in accordance with the bright spot (the bright spot image Br) to move the measurement head 16 in the X direction (the left and right direction) and the Y direction (the up and down direction). At this time, the control portion 28 displays an alignment mark AL as a guide for the alignment on the display surface 35a in addition to the anterior eye part image I with the bright spot image. Further, the control portion 28 may control to start the measurement after the completion of the alignment. The alignment light source 45a is an emitting diode emitting infrared light (940 nm, for example) to prevent the subject from seeing the alignment light source 45a during the alignment by the XY-alignment system 45.

The visual target projection system 42 is configured to project the visual target to place the subject eye E in the visual fixation or fogging state and provide the visual target to the fundus Ef. The visual target projection system 42 includes a display 42a, rotary prisms 42b, 42c, an imaging lens 42d, a moving lens 42e, a relay lens 42f, a field lens 42g, a mirror 42h, and a dichroic filter 42i. The visual target projection system 42 shares the dichroic filter 41b and the objective lens 41a with the observation system 41. The display 42a provides the fixed visual target or a dotted visual target for fixing the visual line of the subject eye E, and provides a subjective examination target for subjectively examining the characteristics of the subject eye E such as the visual acuity value, the correction power or degree (distance power, near distance power). The display 42a displays any images under the control of the control portion 28. The display 42a may be an EL (electroluminescence) display or a liquid crystal display (LCD). The display 42a is provided to move along the optical axis to a position conjugate with the fundus Ef of the subject eye E on the optical path of the visual target projection system 42.

The rotary prisms 42b, 42c are used to adjust the prismatic power and the prism base setting (direction) in a phoria (heterophoria) inspection and are separately rotated by a pulse motor or the like. The prism power is continuously changed when the rotary prisms 42b, 42c are rotated in opposite directions. On the other hand, the prism base setting is continuously changed when the rotary prisms 42b, 42c are rotated integrally in the same direction. The moving lens 42e is driven forward and backward along the optical axis by a drive motor. The visual target projection system 42 can displace the refractive power to the minus side by moving the moving lens 42e toward the subject eye E, and displace the refractive power to the plus side by moving the moving lens 42e away from the subject eye E. Therefore, the visual target projection system 42 can change the providing distance of the visual target (the provided position of the visual target image) displayed on the display 42a by moving the moving lens 42e forward or backward and place the subject eye E in the visual fixation or fogging state. Thereby, the visual target projection system 42 can provide the visual target for the visual fixation or the subjective inspection at any providing distance relative to the subject eye E.

The eye refractive power measurement system 43 projects the measurement luminous flux onto the fundus Ef of the subject eye E and obtains the measurement luminous flux (or reflected luminous flux) reflected by the fundus Ef as a measurement ring image Ri (see FIG. 10) so that the eye refractive power of the corresponding subject eye E can be measured. The eye refractive power measurement system 43 in this embodiment includes a ring luminous flux projection system 43A and a ring luminous flux reception system 43B. The ring luminous flux projection system 43A is configured to project a ring measurement pattern onto the fundus Ef of the subject eye E. The ring luminous flux reception system 43B is configured to detect (receive) the reflected light of the ring measurement pattern from the fundus Ef. The eye refractive power measurement system 43 is not limited to the above configuration of this embodiment. However, the eye refractive power measurement system 43 may have any configuration as long as the system projects the measurement luminous flux onto the fundus Ef of the subject eye E and obtains the measurement luminous flux reflected on the fundus Ef as the measurement ring image Ri. For example, the eye refractive power measurement system 43 may have a configuration that projects a dotted spotlight onto the fundus Ef as the measurement luminous flux and obtains the measurement ring image Ri as the ring luminous flux by receiving the measurement luminous flux reflected on the fundus Ef (the reflected luminous flux) through the ring-shaped slit or a lens.

The ring luminous flux projection system 43A includes a refraction light source unit 43a, a relay lens 43b, a pupil ring diaphragm 43c, a field lens 43d, an open prism 43e which has an opening 43p, and a rotary prism 43f. The ring luminous flux projection system 43A shares the dichroic filter 42i with the visual target projection system 42 and shares the dichroic filter 41b and the objective lens 41a with the observation system 41. The refraction light source unit 43a includes a refractometry measurement light source 43g for a refractometry measurement using LED, for example, a collimator lens 43h, a conical prism 43i, and a ring pattern formed plate 43j, which can move integrally on the optical axis of the eye refractive power measurement system 43 under the control of the control portion 28.

The ring luminous flux reception system 43B includes the opening 43p of the open prism 43e, a field lens 43q, a reflecting mirror 43r, a relay lens 43s, a focusing lens 43t, and a reflecting mirror 43u. The ring luminous flux reception system 43B shares the objective lens 41a, the dichroic filter 41b, the dichroic filter 41e, the imaging lens 41f, and the image sensor 41g with the observation system 41. Also, the ring luminous flux reception system 43B shares the dichroic filter 42i with the visual target projection system 42 and shares the rotary prism 43f and the open prism 43e with the ring luminous flux projection system 43A.

The eye refractive power measurement system 43 in an eye refractive power measurement mode measures the eye refractive power of the subject eye E under the control of the control portion 28 as follows. First, the refractometry (ref) measurement light source 43g of the ring luminous flux projection system 43A is lit, and the refraction light source unit 43a of the ring luminous flux projection system 43A and the focusing lens 43t of the ring luminous flux reception system 43B are moved in the optical axis direction. In the ring luminous flux projection system 43A, the refraction light source unit 43a emits the ring measurement pattern and the measurement pattern travels through the relay lens 43b, the pupil ring diaphragm 43c and the field lens 43d to the open prism 43e. The measurement pattern is reflected on the reflective surface 43v and guided to the dichroic filter 42i through the rotary prism 43f. In the ring luminous flux projection system 43A, the measurement pattern is guided to the objective lens 41a through the dichroic filter 42i and the dichroic filter 41b so that the ring measurement pattern is projected onto the fundus Ef of the subject eye E.

In the ring luminous flux reception system 43B, the ring measurement pattern formed on the fundus Ef is collected by the objective lens 41a and travels through the dichroic filter 41b, the dichroic filter 42i and the rotary prism 43f into the opening 43p of the open prism 43e. In the ring luminous flux reception system 43B, the measurement pattern travels through the field lens 43q, the reflecting mirror 43r, the relay lens 43s, the focusing lens 43t, the reflecting mirror 43u, the dichroic filter 41e, and the imaging lens 41f and the image of the measurement pattern is formed on the image sensor 41g. Thereby, the image sensor 41g detects the image of the ring measurement pattern (also referring to as the measurement ring image Ri) and the measurement ring image Ri is displayed on the display surface 35a of the display 35 (see FIG. 10). The control portion 28 calculates the spherical power S, the cylindrical power C (astigmatic power) and the axial angle Ax (astigmatic axis angle) as the eye refractive power based on the measurement ring image Ri (the image signal from the image sensor 41g) by a known manner method. The calculated eye refractive power is displayed on the display surface 35a under the control of the control portion 28.

In the eye refractive power measurement mode, under the control of the control portion 28, a fixed visual fixation target is displayed on the display 42a in the visual target projection system 42. The luminous flux from the display 42a is projected onto the fundus Ef of the subject eye E through the rotary prisms 42b, 42c, the imaging lens 42d, the moving lens 42e, the relay lens 42f, the field lens 42g, the mirror 42h, the dichroic filter 42i, the dichroic filter 41b, and the objective lens 41a. The examiner or the control portion 28 executes the alignment while the subject keeps the visual fixation to the fixed visual fixation target, and the moving lens 42e is moved to the far point of the subject eye E based on the result of the preliminary measurement of the eye refractive power (refraction) and then to a position where the subject cannot focus on the target in the fogging state. Thereby, the subject eye E is set to be an adjustment inactive state where the crystalline lens of the subject eye E cannot be adjusted, and the eye refractive power of the subject eye E is measured in the adjustment inactive state.

It should be noted that the detailed explanations for the configurations of the eye refractive power measurement system 43, the Z-alignment system 44, the XY-alignment system 45 and the kerato system 46, and the principles of the measurement for the eye refractive power (refraction), the subjective examination and the corneal shape (kerato) are omitted since such configurations and the principals are known in the art.

In the ophthalmologic apparatus 10, the eye information obtaining portion 21 obtains the information on the corresponding subject eye E while executing an auto-alignment under the control of the control portion 28. Specifically, based on the alignment information from the Z-alignment system 44 and the XY-alignment system 45, the control portion 28 calculates an amount of movement (alignment information) which brings the distance between the eye information obtaining portion 21 and the subject eye E to a predetermined operation distance while aligning the optical axis L of the eye information obtaining portion 21 (its optical system) with the axis of the subject eye E. Here, the operating distance is a default value which is also referred to as a working distance, and also a distance between the eye information obtaining portion 21 and the subject eye E to properly measure the characteristics of the subject eye E by using the eye information obtaining portion 21. The control portion 28 drives the drive mechanism 15 in accordance with the amount of the movement to move the eye information obtaining portion 21 relative to the subject eye E and executes the alignment of the eye information obtaining portion 21 (the measurement head 16) in X, Y and Z directions relative to the corresponding subject eye E.

Then, the control portion 28 drives the eye information obtaining portion 21 to obtain various eye information on the subject eye E. In the ophthalmologic apparatus 10, the examiner may manually operate the examiner controller 31 to align the eye information obtaining portions 21 relative to the subject eyes E and to drive the eye refractive power measurement systems 43 to obtain the various information on the subject eyes E. When the various information on the subject eyes E is obtained in the ophthalmologic apparatus 10, the subject may operate the subject controller 32 to assist the obtaining of the information. The alignments in the X, Y, and Z directions match the center of each guide groove in the Y-axis rotary drive portion 24 and the X-axis rotary drive portion 25 with the eyeball rotation point O of the subject eye E. Accordingly, each of the measurement heads 16 can rotate about the eyeball rotation point O in the rotation direction about the Y direction (Y-axis) and the rotation direction about X direction (X-axis). Then, the control portion 28 can obtain the three-dimensional position of the eyeball rotation point O of each subject eye E based on the position of each measurement head 16 for which the alignments in X, Y, and Z directions executed.

The ophthalmologic apparatus 10 may execute the auto-alignment of the eye information obtaining portion 21 by using the two cameras 27, i.e. the subject eye images Ie from the cameras 27. In this case, the control portion 28 detects the common characteristic position between the subject eye images Ie from the respective two cameras 27. For example, in case where the characteristic position is the bright spot image Br formed by the XY-alignment system 45, the control portion 28 obtains coordinates of the bright spot image Br in each of the subject eye images Ie and calculates the three-dimensional position of the bright spot image Br (i.e. the subject eye E) by known trigonometry using the obtained coordinates, the positions and angles of the two cameras 27, the optical characteristics and the like. Then, based on the calculated three-dimensional position of the subject eye E, the control portion 28 calculates the amount of movement (alignment information) which brings the distance between the eye information obtaining portion 21 and the subject eye E to the predetermined operation distance (working distance) while aligning the optical axis L of the eye information obtaining portion 21 (its optical system) with the axis of the subject eye E and controls the drive mechanism 15 based on the calculated amount of the movement. The control portion 28 drives the drive mechanism 15 in accordance with the calculated amount of the movement to move the eye information obtaining portion 21 relative to the subject eye E and executes the auto-alignment of the eye information obtaining portion 21 by using the two cameras 27.

The control portion 28 includes a reference calculator 28b and an inclination calculator 28c. The reference calculator 28b is configured to calculate the three-dimensional position of the reference position (i.e. three-dimensional reference position Pb, see FIG. 7) in the subject eye E based on the two subject eye images Ie captured by the two cameras 27 for the subject eye E. The reference position of one subject eye E is the same location as that of the other subject eye E. Each of the reference positions can be photographed by the two cameras 27. In this embodiment, the reference position is the bright spot image Br which is the virtual image of the bright spot drawn by the XY-alignment system 45. The inclination calculator 28c is configured to obtain inclination information Is based on the three-dimensional reference positions Pb in both subject eyes E obtained by the reference calculator 28b. The inclination information Is shows the inclination of the relative positions of both subject eyes.

First, the reference calculator 28b obtains the positions of the bright spot images Br in the two subject eye images Ie of each subject eye E captured by the two cameras 27 from two different directions. A method for obtaining the position of the bright spot image Br in each subject eye image Ie may be selected from known methods. In each of the subject eyes E, the spot-like virtual image (Purkinje image) is drawn inside the cornea Ec (i.e. at a position half the radius of curvature r of the cornea inward from the corneal vertex Et) when the parallel luminous flux enters from the alignment light source 45a. The Purkinje image is obtained (captured) as the bright spot image Br in each of the subject eye images Ie (see FIG. 6). In this embodiment, the alignment light source 45a is for the infrared light. Accordingly, the position of the bright spot image Br based on the reflected light from the alignment light source 45a can be easily and accurately obtained by extracting only the signal in the infrared light region from the output signal of both cameras 27.

The reference calculator 28b obtains an image area (bright spot area) corresponding to the bright spot image Br in each of the subject eye images Ie based on the distribution of pixel values (luminance values, etc.), for example. Generally, the bright spot area can be obtained by searching the high brightness image area since the bright spot image Br is drawn with a higher brightness than others. Considering the shape of each of the bright spot images Br is substantially circular, the bright spot area may be obtained by searching the substantially circular high brightness image area.

Next, the reference calculator 28b obtains the center of the obtained bright spot area. Since the bright spot image Br is substantially circular as mentioned above, the reference calculator 28b approximates the boundary coordinates of the bright spot area with an ellipse and calculates the center of the bright spot approximate ellipse. First, the reference calculator 28b obtains coefficients a, b, c, d and h in a general formula of the ellipse shown in the following formula I from the boundary coordinates of the bright spot area by the method of least squares.

[Formula I]

$$ax^2+by^2+cx+dy+1+hxy=0 \qquad (1)$$

Next, the reference calculator 28b obtains the central coordinate of the bright spot approximate ellipse by the following formula II using the obtained coefficients in the general formula I of the ellipse. The central coordinate of the bright spot approximate ellipse by the following formula II is the coordinate of the bright spot image Br in each of the subject eye images Ie.

[Formula II]

$$\text{(CENTRAL COORDINATE)} = (\overline{X}, \overline{Y}) \qquad (2)$$

$$\overline{X} = \frac{hd - 2bc}{4ab - h^2}, \overline{Y} = \frac{hc - 2ad}{4ab - h^2}$$

It should be noted that the reference calculator 28b may obtain the gravity center of the bright spot area, and use the obtained gravity center as the coordinate of the bright spot image Br in each of the subject eye images Ie.

Then, the reference calculator 28b calculates the three-dimensional position of the bright spot image Br as the reference position for each subject eye E based on the positions of the two cameras 27 which have captured the two subject eye images Ie and the coordinates of the bright spot images Br in the two subject eye images Ie. This process will be described with reference to FIG. 6.

Figure 6:
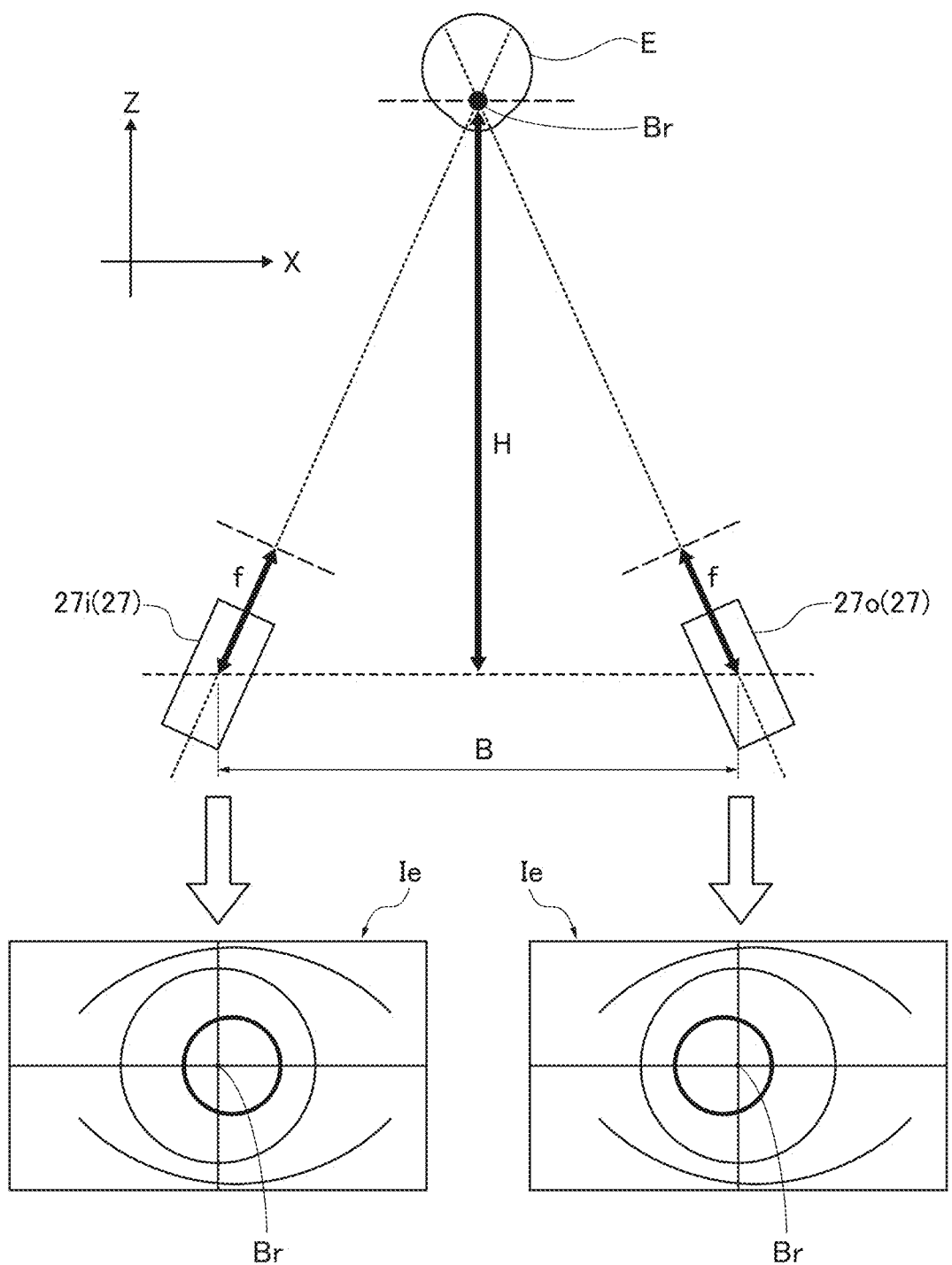
FIG. 6 is an explanatory view illustrating an obtaining of the three-dimensional position of the characteristic position of the subject eye by a pair of cameras.

FIG. 6 shows the positional relation among the subject eye E, the outer camera 27o and the inner camera 27i, and the subject eye images Ie captured by the cameras 27o, 27i. In FIG. 6, the positional relation among the subject eye E and the cameras 27o, 27i in the Y direction (the vertical direction) is not shown. The position of the subject eye E and the positions of the cameras 27o, 27i may be at the same or different height in the Y direction. Now, the distance between the outer camera 27o and the inner camera 27i is defined as a baseline length B and the distance between the baseline length B and the bright spot image Br in the subject eye E is defined as a photographing distance H. In addition, the outer camera 27o and the inner camera 27i have the same configuration, and a distance between the lens center and the image sensor (screen plane) in the each of the cameras 27o, 27i is defined as a screen distance f (substantially equal to the focal length).

The resolution of the subject eye images Ie by the outer camera 27o and the inner camera 27i can be expressed by the following formulas. In the formulas, Δp is the pixel resolution in the cameras 27.

Resolution in the X and Y directions(planar resolution): Δxy=H×Δp/f

Resolution in the Z direction(depth resolution): Δz=H×H×Δp/(B×f)

In this way, the deflection in the Z direction can be detected as the deflection in the pixel positions in the subject eye images Ie by the two cameras 27, and accordingly, the position in the Z direction can be detected in accordance with the pixel resolutions of both cameras 27.

The reference calculator 28b obtains the three-dimensional position of the bright spot image Br by applying the known trigonometry considering the positional relation shown in FIG. 6 to the positions of the outer camera 27o and the inner camera 27i, which have been already known, and to the coordinates of the bright spot images Br in the two subject eye images Ie, and sets the obtained three-dimensional position as the three-dimensional reference position Pb for each of the subject eyes E.

Figure 7:
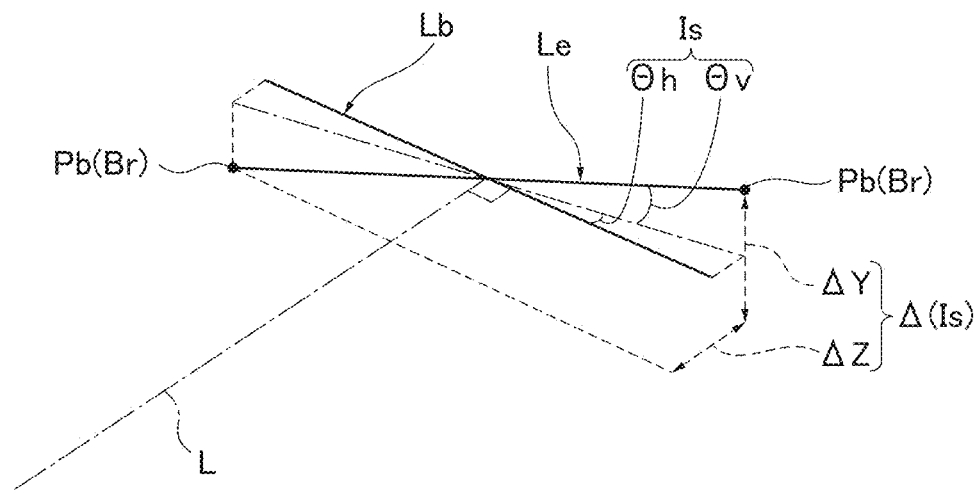
FIG. 7 is an explanatory view illustrating an example of inclination information.

The inclination calculator 28c obtains the inclination information Is (see FIG. 7) based on the three-dimensional reference positions Pb (the three-dimensional positions of the bright spot images Br) of both subject eyes E obtained by the reference calculator 28b. The inclination information Is indicates the inclination of the relative positions of the subject eyes E. In this embodiment, the inclination information Is is indicated with the amount of displacement Δ of the three-dimensional reference position Pb of one of the subject eyes E relative to the three-dimensional reference position Pb of the other of the subject eyes E as shown in FIG. 7. The inclination calculator 28c obtains an amount of displacement (Z-displacement) Δz and an amount of displacement (Y-displacement) Δy to set the inclination information Is. The amount of displacement (Z-displacement) Δz indicates the amount of displacement Δ in the Z direction (the front and rear direction) and the amount of displacement (Y-displacement) Δy indicates the amount of displacement Δ in the Y direction (the up and down direction).

The inclination calculator 28c may indicate the inclination of an eye-axis Le relative to a reference axis Lb. The eye-axis Le connects the three-dimensional reference positions Pb of both subject eyes E as the inclination information Is. The reference axis Lb is a straight line that extends horizontally and perpendicular to the optical axis L of the eye information obtaining portion 21. In this case, the inclination calculator 28c may obtain a horizontal inclination angle θh and a vertical inclination angle θv to set the inclination information Is. The horizontal inclination angle θh is an angle between the eye-axis Le and the reference axis Lb on a horizontal plane. The vertical inclination angle θv is an angle between the eye-axis Le and the reference axis Lb on a vertical plane. Note that the inclination information Is only needs to indicate the inclination of the relative positions of the two subject eyes E and is not limited to the configuration in this embodiment.

Figure 8:
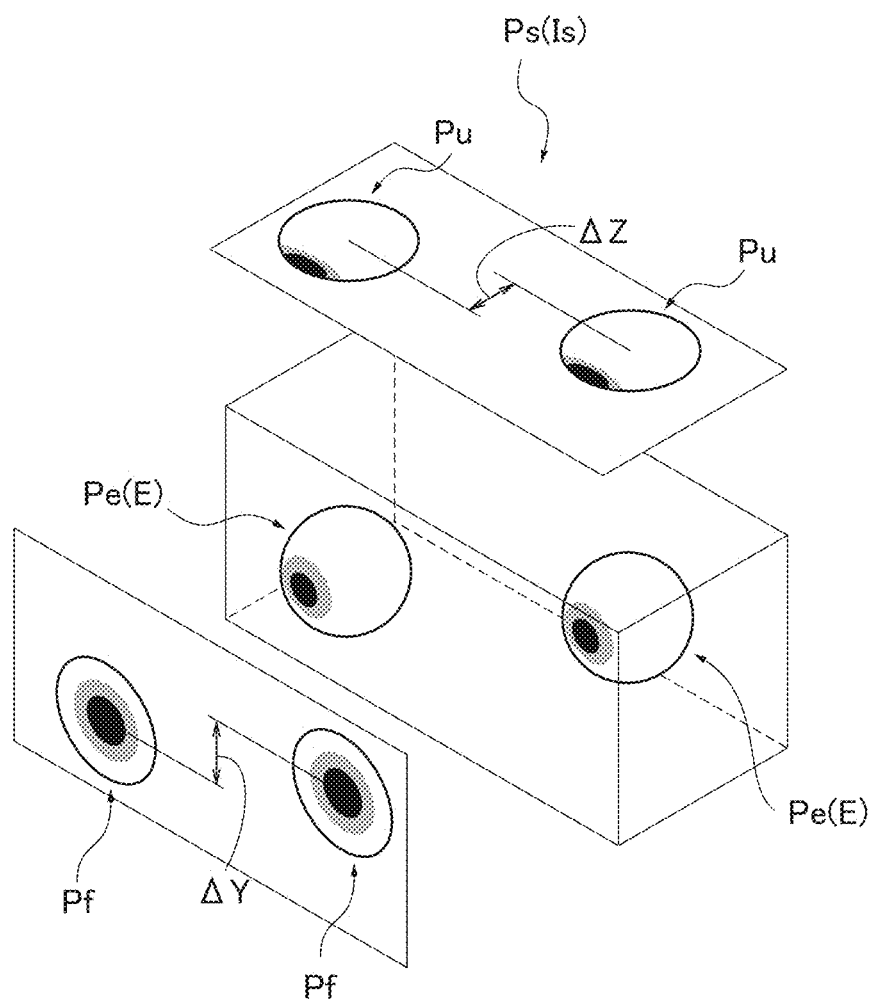
FIG. 8 is an explanatory view illustrating an example of an inclination notification image.

The inclination calculator 28c in this embodiment generates an inclination notification image Ps to display the inclination information Is on the display 35 (the examiner controller 31). The inclination notification image Ps visually displays the inclination information Is to facilitate the understanding of the inclination. FIG. 8 illustrates an example of the inclination notification image Ps. The inclination notification image Ps includes three-dimensional images Pe, front images Pf and upper images Pu of the subject eyes E in a pseudo-three-dimensional space. Each of the three-dimensional images Pe three-dimensionally shows the subject eye E. Each of the front images Pf shows the subject eye E from the front side thereof. Each of the upper images Pu shows the subject eye E from the upper side thereof. The inclination notification image Ps shows the three-dimensional images Pe of the subject eyes E which indicate the positional relation of the subject eyes, the front images Pf forward of the three-dimensional image Pe, and the upper images Pu above the three-dimensional images Pe. The inclination notification image Ps displays the front images Pf together with the Y-displacement Δy and the upper images Pu together with the Z displacement Δz. Thereby, the inclination notification image Ps facilitates the sensuous understanding of the positional relation of the subject eyes E and the accurate understanding of the inclination direction and the inclination amount. It should be noted that the inclination notification image Ps may display the front images Pf together with the vertical inclination angle θv and the upper images Pu together with the horizontal inclination angle θh. The inclination notification image Ps is not limited to the one in this embodiment but is required only to notify the inclination information Is. Further, the inclination notification image Ps may additionally display information (distance between pupils, for example) which indicates the positional relation of the subject eyes E.

The control portion 28 notifies the inclination information Is by displaying the inclination notification image Ps generated by the inclination calculator 28c on the display 35 (the examiner controller 31). Accordingly, the display 35 functions as a notification portion. It should be noted that the notification portion is not limited to the one in this embodiment. The notification portion only needs to notify the inclination information Is generated by the inclination calculator 28c and accordingly, other displays, speakers or voice notification may be used as the notification portion.

Figure 9:
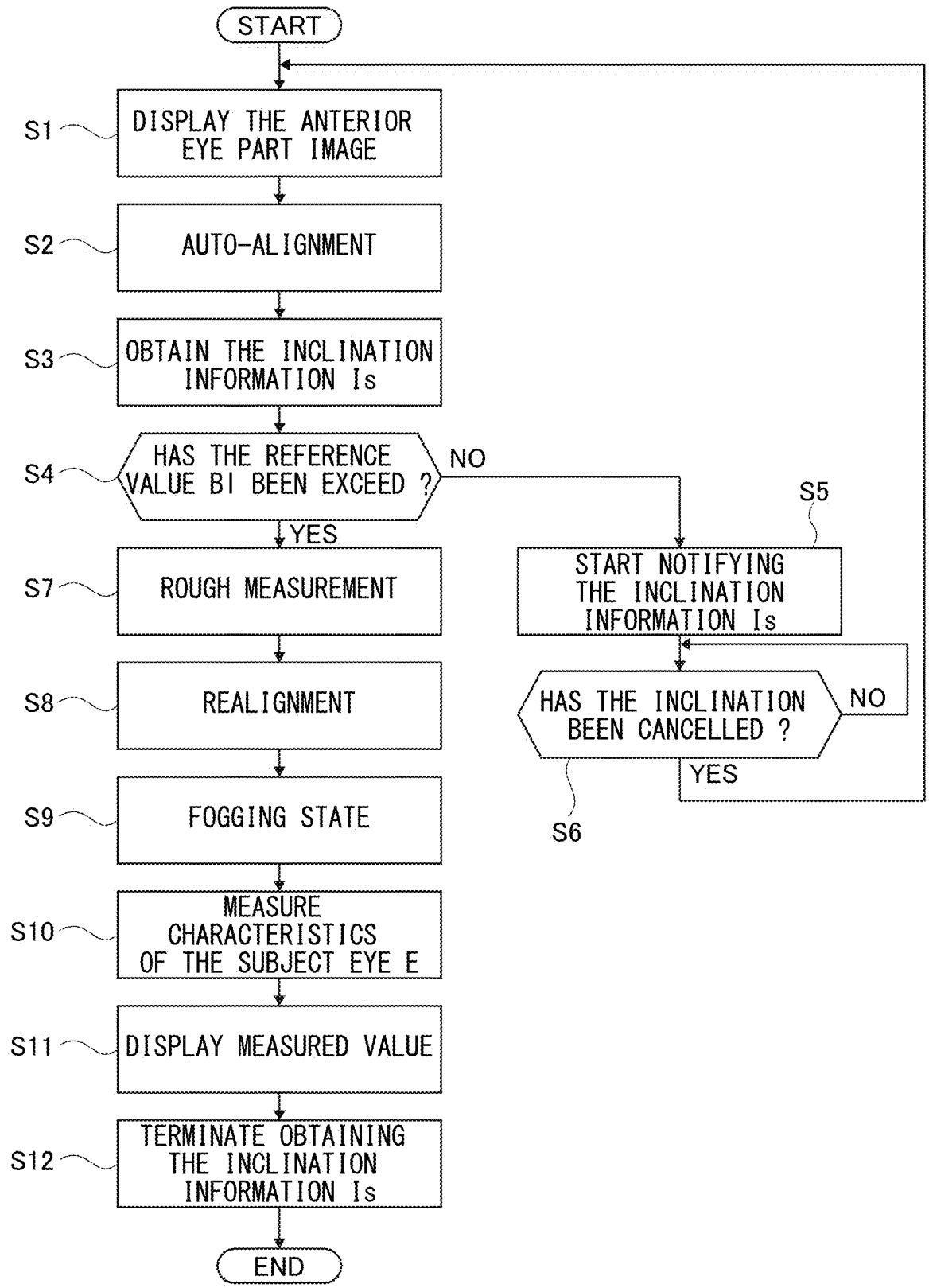
FIG. 9 is a flowchart showing an eye information obtaining process (eye information obtaining method) executed by a control portion of the ophthalmologic apparatus.

The control portion 28 may control to notify the inclination information Is (the inclination notification image Ps) when the inclination of the relative positions of the subject eyes E exceeds a reference value Bl (see FIG. 9). For example, the reference value Bl may be set to (the amount or degree of) the inclination of the relative positions of the subject eyes E that are considered to affect the obtained information of the subject eyes E. The control portion 28 determines whether to notify the inclination information Is by determining whether the inclination of the relative positions of the subject eyes E indicated by the inclination information Is exceeds the reference value Bl or not. With the above configuration, the inclination information Is is notified only when the correction of the inclination is required as obtaining the information on the subject eyes E, which can prevent annoyance related to the notification or the like.

Further, the control portion 28 may notify the inclination information Is (the inclination notification image Ps) regardless of the degree of the inclination of the relative positions of the subject eyes E and output predetermined waring information to the output portion when the inclination exceeds the reference value Bl. The output portion includes the display 35, an audio output portion (not shown) and the like. In the case where the display 35 is used as the output portion, the control portion 28 displays a warning message on the display 35 (the display surface 35a). For example, the warning message includes predetermined character string information, image information, a popup window and the like. In the case where the audio output portion is used as the output portion, the control portion 28 controls the audio output portion to output predetermined audio information, warning sound or the like.

Next, an eye information obtaining process (a method for obtaining eye information) will be described with reference to FIG. 9. The eye information obtaining process (the method for obtaining eye information) is an example of obtaining the inclinations of the subject eyes E and notifying them when obtaining information on the subject eyes E by using the ophthalmologic apparatus 10. The control portion 28 executes the eye information obtaining process based on the program stored in the storage portion 33 or the internal memory 28a. Hereinafter, each step (process) of the flowchart shown in FIG. 9 will be described. The flowchart shown in FIG. 9 starts when the ophthalmologic apparatus 10 is activated. The activation of the ophthalmologic apparatus 10 launches the browser or application of the examiner controller 31, turns on the display surface 35a and starts obtaining the eye information in the input portion 35b. At this time, the subject sits on the chair or the like and puts his or her forehead on the forehead holder 17. In the flowchart shown in FIG. 9 of this embodiment, each step (process) is simultaneously executed in both measurement heads 16 (both eye information obtaining portions 21) to simultaneously measure both subject eyes in the binocular vision state. In the flowchart shown in FIG. 9 of this embodiment, the moving image of a front subject eye image If is displayed on the display surface 35a, which will be described later. However, the displayed image is not limited to the moving image but may be a still image or a frame advance image.

In the flowchart shown in FIG. 9 of this embodiment, the eye refractive power is used as the information on the subject eyes E as an example and accordingly, the eye refractive power measurement system 43 executes the measurement of the subject eyes E.

In Step S1, the image of the anterior eye part of the subject eye E is displayed on the display surface 35a of the display 35, and the process proceeds to Step S2. In Step S1, the moving image of the front subject eye image If from one of the cameras 27 is displayed on the display surface 35a as the anterior eye part image. The front subject eye image If is an image obtained by converting the subject eye image Ie captured by one of the cameras 27 to an image viewed from a virtual viewpoint in front of the subject eye E. The control portion 28 generates the front subject eye image If viewed from the virtual viewpoint by executing the conversion process. In the conversion process, all the coordinate values of the output pixels are formed by multiplying the coordinate values of each pixel of the subject eye image Ie input from one of the cameras 27 by various coefficients based on the angle of the camera 27 and the like. In Step S1, the anterior eye part image I (moving image) obtained in the observation system 41 may be displayed on the display surface 35a.

In Step S2, the auto-alignment is executed and the process proceeds to Step S3. In Step S2, the auto-alignment of the eye information obtaining portion 21 is executed by using both cameras 27, i.e. the subject eye images Ie (data) from the cameras 27. At this time, the moving images of the subject eye images Ie of the subject eye E by both cameras 27 are displayed on the display surface 35a in Step S2. In Step S2, the auto-alignment may be executed by the Z-alignment system 44 and the XY-alignment system 45 together with Step S8, which will be described later.

In Step S3, obtaining the inclination information Is which indicates the inclination of the relative positions of the subject eyes E is started and the process proceeds to Step S4. In Step S3, the inclination information Is is obtained by using the subject eye images Ie (its data) from both cameras 27. Therefore, the inclination information Is is obtained in real-time after Step S3.

In Step S4, it is determined whether the inclination of the relative positions of the subject eyes E shown by the inclination information Is has exceeded the reference value Bl or not. The process proceeds to Step S7 in the case of YES, or the process proceeds to Step S5 in the case of NO. In Step S4, the determination is executed to determine whether the inclination information Is should be notified or not.

In Step S5, the notification of the inclination information Is is started and the process proceeds to Step S6. In Step S5, the notification of the inclination information Is obtained in Step S3 is started. In this embodiment, the inclination notification image Ps of the subject eyes E is displayed on the display surface 35a. In Step S5 of this embodiment, it is also notified that the inclination of the relative positions of the subject eyes E exceeds the reference value Bl. This notification may be displayed with letters, symbols or the like on the display surface 35a or on another display portion or may be an audio notification, for example. The notification is not limited to the one in this embodiment but the notification of the inclination information Is (display of the inclination notification image Ps) may always be executed in real-time after Step S3. In the case of the real-time notification, the start of the notification of the inclination information Is can be omitted in Step S5.

In Step S6, it is determined whether the inclination of the relative positions of the subject eyes E has been canceled or not. The process returns to Step S1 in the case of YES, or the process repeats Step S6 in the case of NO. In Step S6, it is determined whether the inclination of the relative positions of the subject eyes E has become smaller than the reference value Bl in the inclination information Is obtained by using the subject eye images Ie (its data) from both cameras 27. In Step S6, the examiner recognizes that both subject eyes E incline by the notification of the inclination information Is in Step S5 and adjusts the inclination of the face (or head) of the subject in accordance with the inclination information Is. The process returns to Step S1 after the inclination of the subject eyes E is adjusted in Step S6. Alternatively, in Step S6, the process may return to Step S1 when the examiner inputs the operation to adjust the inclination of the face of the subject to the input portion 35b, or the like.

Figure 10:
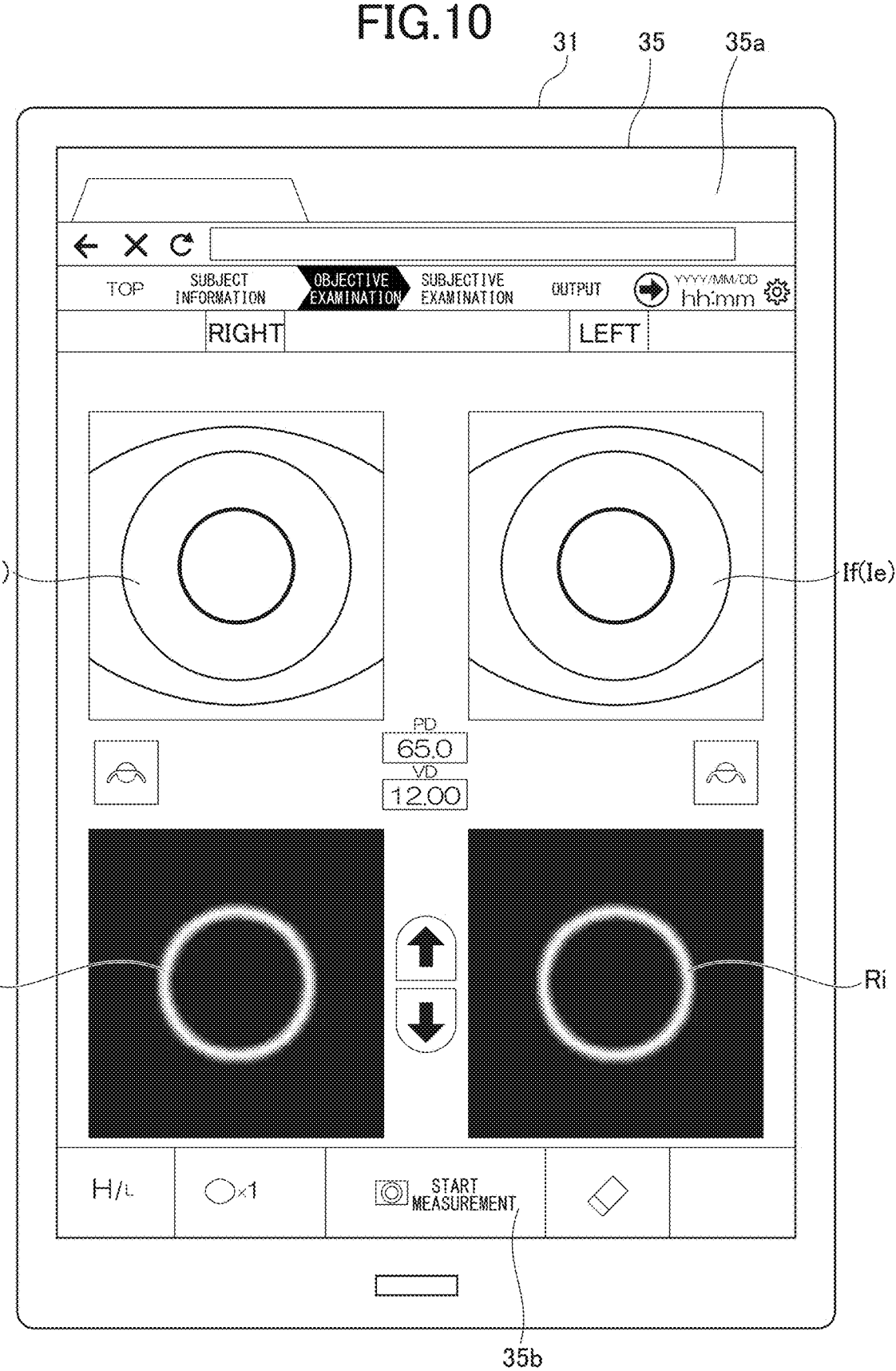
FIG. 10 is a view illustrating a display screen of the ophthalmologic apparatus which shows the eye information.

In Step S7, a rough measurement is executed by using the eye refractive power measurement system 43 and the process proceeds to Step S8. The rough measurement is to preliminarily and roughly measure the eye refractive power of the subject eyes E to determine the movement amount of the moving lens 42e of the visual target projection system 42, the refraction light source unit 43a of the ring luminous flux projection system 43A and the focusing lens 43t of the ring luminous flux reception system 43B. In Step S7, the moving lens 42e, the refraction light source unit 43a and the focusing lens 43t are arranged at a 0D (diopter) position. Then, the subject eyes E are set in the visual fixation state in the visual target projection system 42 and the ring luminous flux projection system 43A of the eye refractive power measurement system 43 projects the ring measurement pattern onto the fundus Ef of the subject eyes E. Then, in Step S7, the image sensor 41g detects the measurement ring image Ri of the ring measurement pattern via the ring luminous flux reception system 43B and the eye refractive power is measured based on the measurement ring image Ri while the measurement ring image Ri is displayed on the display surface 35a of the display 35. Further, in Step S7, the front subject eye image If (moving image) from one of the cameras 27 for each subject eye E is displayed on the display surface 35a together with the measurement ring image Ri as shown in FIG. 10. Specifically, the front subject eye images If (moving images) and the measurement ring images Ri of both subject eyes E are displayed on the display surface 35a.

In Step S8, the auto-alignment (realignment) is executed and the process proceeds to Step S9. In Step S8, the auto-alignment is executed in the same manner as in Step S2.

In Step S9, the visual target projection system 42 places the subject eyes E in the fogging state and the process proceeds to Step S10. In Step S9, the subject eyes E are placed in the fogging state by the visual target projection system 42 after moving the focusing lens 43t based on the eye refractive power from the rough measurement in Step S7. Accordingly, the subject eyes E are placed in the adjustment inactive state. At this time, the front subject eye images If are displayed on the display surface 35a in Step S9.

In Step S10, the characteristics of the subject eyes E are measured by using the eye refractive power measurement system 43 and the process proceeds to Step S11. In Step S10, the refraction light source unit 43a and the focusing lens 43t of the eye refractive power measurement system 43 are moved in accordance with the eye refractive power measured by the rough measurement in Step S7, and the measurement ring images Ri are detected by the eye refractive power measurement system 43 in relation to the subject eyes E in the fogging state (the adjustment inactive state). Further, in Step S10, the spherical power, the cylindrical power and the axis angle as the eye refractive power are calculated by a known method based on the measurement ring images Ri obtained by the eye refractive power measurement system 43. At this time, the front subject eye images If are displayed on the display surface 35*a* with the measurement ring images Ri in Step S10.

In Step S11, a measured value is displayed and the process proceeds to Step S12. In Step S11, the eye refractive power (the spherical power, the cylindrical power, and the axis angle) of both subject eyes E measured in Step S10 are displayed on the display surface 35*a*.

In Step S12, the obtaining of the inclination information Is started in Step S3 is ended and the eye information obtaining process is terminated. In the case where the notification of the inclination information Is (display of the inclination notification image Ps) is executed in real-time, the notification of the inclination information Is is also terminated in Step S12. It should be noted that in the flowchart shown in FIG. 9, the obtaining of the inclination information Is may be ended before Step S7 since the determinization by using the inclination information Is is not executed after Step S7.

The ophthalmologic apparatus 10 can measure the eye refractive power of the subject eyes E. The ophthalmologic apparatus 10 measures the eye refractive power of both subject eyes E in the binocular vision state. Therefore, the ophthalmologic apparatus 10 can measure the eye refractive power of both subject eyes E which are in the more natural state and reduce the measurement time compared to the measurement executed one by one.

The ophthalmologic apparatus 10 of the present disclosure can obtain the information on the subject eyes E by the eye information obtaining process described above. The ophthalmologic apparatus 10 can obtain the inclination information Is based on the subject eye images Ie from the cameras 27 which are provided separately from the eye information obtaining portions 21. Accordingly, the inclination notification image Ps can also be displayed to notify the inclination information Is. Thereby, the examiner can understand the inclination of the relative positions of the subject eyes E in real-time while obtaining the information on the subject eyes E. Therefore, when the obtained information is undesirable, it is easy to determine whether the undesirable information is caused by that the lines of sight of the subject eyes E are not directed to appropriate directions. At this time, the ophthalmologic apparatus 10 obtains the inclination information Is based on the subject eye images Ie from the cameras 27 and accordingly, the ophthalmologic apparatus 10 can accurately obtain the inclination information Is. This is because the ophthalmologic apparatus 10 obtains the three-dimensional positions (the three-dimensional reference positions Pb) of the reference positions (the bright spot images Br) in the subject eyes E based on the subject eye images Ie from the cameras 27 so that the displacement in the Z direction (the front and rear direction) can be recognized as the displacement in the X direction in the subject eye images Ie, and the displacement in the Z direction can be detected by pixel resolution in the cameras 27.

The ophthalmologic apparatus 10 notifies the obtained inclination information Is but does not correct the inclination in the obtained information on the subject eyes E by a correction means, unlike the prior art. The conventional ophthalmologic apparatus corrects the information on the subject eyes E which has been obtained while the subject inclines his or her head (face) so that the conventional ophthalmologic apparatus executes the measurement in the state where the counter-rotation of the eyeballs that rotates the eyeballs to cancel the inclination occurs. Therefore, in the conventional ophthalmologic apparatus, even corrected information on the subject eyes by canceling the inclination may be affected by the counter-rotation of the eyeballs and consequently, the corrected information may differ from the information on the subject eyes in the natural state which is not affected by the counter-rotation of the eyeballs.

On the other hand, the ophthalmologic apparatus 10 notifies the obtained inclination information Is. Thereby, the aspects (direction or degree) of the inclination of the relative positions of the subject eyes E can be recognized, the inclination of the head (face) of the subject can be easily corrected and accordingly, the information on the subject eyes E in the natural state can be obtained. Particularly, the ophthalmologic apparatus 10 in this embodiment notifies the obtained inclination information Is when the inclination of the relative positions of the subject eyes E exceeds the reference value Bl. Accordingly, the information on the subject eyes E in the natural state can be obtained without annoyance related to the notification or the like. Therefore, the ophthalmologic apparatus 10 can easily obtain the information on the subject eyes E in the natural state.

According to the ophthalmologic apparatus 10 in this embodiment of the present disclosure, the following effect can be achieved.

The ophthalmologic apparatus 10 includes the eye information obtaining portions 21, each of the eye information obtaining portions 21 corresponding to each of the subject eyes E of the subject and configured to obtain information on each of the subject eyes E, and the imaging portions (cameras 27 in this embodiment), each of the imaging portions corresponding to each of the eye information obtaining portions 21 and configured to capture the image of each of the subject eyes E. Further, the ophthalmologic apparatus 10 includes the reference calculator 28*b* configured to obtain the three-dimensional reference position Pb in each of the subject eye images Ie captured by each of the imaging portions, the inclination calculator 28*c* configured to obtain the inclination information Is indicating the inclination of the relative positions of the subject eyes E from the two three-dimensional reference positions Pb, and the notification portion (the display 35 in this embodiment) configured to notify the inclination information Is. According to the ophthalmologic apparatus 10, the inclination of the relative positions of the subject eyes E can be recognized by the notification of the obtained inclination information Is. Therefore, the inclination of the head (or face) of the subject can be easily corrected and the information on the subject eyes E can be easily obtained in the natural state.

In the ophthalmologic apparatus 10, the notification portion (the display 35) notifies the inclination information Is when the inclination information Is exceeds the reference value Bl while each of the eye information obtaining portions 21 obtains the information on the subject eye E. Specifically, the ophthalmologic apparatus 10 notifies the inclination information Is only when it is considered that the obtained information on the subject eyes E may be affected, for example. Therefore, the information on the subject eyes E in the natural state can be easily obtained without any annoyance related to the notification or the like.

The ophthalmologic apparatus 10 further includes reference projection portions (the XY-alignment systems 45 in this embodiment) configured to respectively correspond to each of the subject eyes E and to project a light for forming the bright spot image Br onto the anterior eye part of each subject eye E. The reference calculator 28b obtains the three-dimensional positions of the bright spot images Br in the subject eye images Ie and sets the obtained three-dimensional positions as the three-dimensional reference positions Pb for the subject eyes E. In the ophthalmologic apparatus 10, the bright spot images Br are formed under the same conditions regardless of the difference in the characteristics of the left and right subject eyes E such as the appearance shapes and the like. Therefore, the inclination information Is (the inclination of the relative positions of the subject eyes E) can be more appropriately obtained by setting the three-dimensional positions as the three-dimensional reference positions Pb for the subject eyes E.

In the ophthalmologic apparatus 10, each of the two imaging portions includes two or more imaging devices (the two cameras 27 in this embodiment). Each of the imaging devices is configured to capture images of the anterior eye part of the corresponding subject eye E from a different direction from others. The reference calculator 28b obtains the three-dimensional positions of the bright spot images Br based on the plurality of subject eye images Ie captured by the imaging devices. The ophthalmologic apparatus 10 sets, as the three-dimensional reference positions Pb, the three-dimensional positions of the bright spot images Br obtained by using the virtual images (Purkinje images) by the corneal surface reflection drawn by the light from the XY-alignment system 45. Therefore, the inclination information Is (the inclination of the relative positions of the subject eyes E) can be more accurately obtained. Particularly, in the ophthalmologic apparatus 10, each of the eye information obtaining portions 21 includes the two cameras 27 which are respectively arranged at different sides of the optical axis L. Therefore, the ophthalmologic apparatus 10 can accurately obtain the inclination information Is while the eye information obtaining portions 21 are obtaining the information on the subject eyes E.

Therefore, the ophthalmologic apparatus 10 according to this embodiment of the present disclosure can easily obtain the information on the subject eyes E in the natural state.

The ophthalmologic apparatus of the present disclosure has been described with reference to the embodiment. However, the above specific configurations are not limited to the ones in this embodiment and design changes and additions are allowed without departing from the scope of the claimed inventions.

For example, in the above embodiment, the reference calculator 28b obtains the three-dimensional position of the bright spot image Br for each of the subject eyes E by using the two different subject eye images Ie captured by the two cameras 27 at the same time and the obtained three-dimensional position is set as the three-dimensional reference position Pb. However, the three-dimensional reference position Pb may be obtained by using other configurations. For example, the reference calculator 28b may obtain the three-dimensional position of the bright spot image Br for each of the subject eyes E based on aspects of the bright spot images Br in the subject eye images Ie, i.e. the positions of the bright spot images Br, focus conditions or the like. In this case, the control portion 28 may calculate the amount of movement (the alignment information) by which distances between the eye information obtaining portions 21 and the subject eyes E reach predetermined operation distances while aligning the optical axes L of the eye information obtaining portions 21 (its optical system) with the axes of the subject eyes E, based on the alignment information from the Z-alignment system 44 and the XY-alignment system 45. At this time, the reference calculator 28b executes the alignment in the Z direction along the optical axis L of the optical system in the eye information obtaining portion 21 for each of the subject eyes E by the horizontal drive portion 23 moving the measurement head 16 in the Z direction (the front and rear direction) such that the ratio between the distance between the two bright spot images on the image sensor 41g from the alignment light source 44a and the diameter of the kerato ring image is within a predetermined range. Further, the reference calculator 28b may execute the alignment in the Z direction by adjusting the position of the right measurement head 16R such that the bright spot image is focused by the alignment light source 45a. The reference calculator 28b can calculate the three-dimensional position of each subject eye E by adding the operation distance to the position of the eye information obtaining portion 21 (the measurement head 16) and set the three-dimensional position as the three-dimensional reference position Pb.

Further, in this embodiment, the reference calculator 28b obtains the three-dimensional position of the bright spot image Br for each of the subject eyes E to set the three-dimensional reference position Pb. However, the reference position is not limited to the one in this embodiment and may be another location in each of the two subject eye images Ie of the subject eye E captured by the two cameras 27 from the different directions. For example, the pupil center position may be set as the reference position. In this case, a method for obtaining the pupil center position may be properly selected from known methods. For example, the reference calculator 28b may obtain an image area (pupil area) corresponding to the pupil of the subject eye E in each of the two subject eye images Ie based on the distribution of pixel values (luminance values, etc.). In general, the pupil is drawn with a lower luminance than other parts, so that the pupil area can be obtained by searching for the lower luminance image area. Considering that the shape of the pupil is approximately circular, the pupil area may be obtained by searching for an image area having a substantially circular shape and lower luminance. Similar to the bright spot area (the bright spot image Br), the reference calculator 28b may obtain the center position of the obtained pupil area to set the coordinate of the pupil center position in each of the subject eye images Ie and calculate the three-dimensional position of the pupil center position for each of the subject eyes E based on the two coordinates and the positions of the two cameras 27. Thereby, the pupil center position as the reference position may be set as the three-dimensional reference position Pb by the reference calculator 28b.

Further, in this embodiment, the control portion 28 notifies the inclination information Is (the inclination notification image Ps) when the inclination of the relative positions of the subject eyes E exceeds the reference value Bl. However, the control portion 28 is not limited to the one shown in this embodiment. The control portion 28 may notify the inclination of the relative positions of the subject eyes E constantly or in multiple scenes. The control portion 28 may determine whether to notify or not by using the plurality of reference values Bl. In the case where the plurality of reference values Bl are used, a first reference value which is stricter and a second reference value which is milder may be used, for example. In the flowchart shown in FIG. 9, the inclinations of the subject eyes E may be determined by using the first reference value after the auto-alignment (Step S2) and before the rough measurement (Step S7), and the inclinations of the subject eyes E may be determined by using the second reference value in other steps or processes, for example. This is based on the following reasons. The alignment may be executed while the subject eyes E incline after the auto-alignment and before the rough measurement and the inclination of the subject eyes E significantly affects the accuracy of the information on the subject eyes E. Accordingly, it is preferable to strictly determine the inclination. After the alignment in the natural state, on the other hand, the possibility that the subject moves his or her head (face) is small or it is assumed that the subject may move greatly if the subject needs to move his or her head (face). Accordingly, issues are unlikely to occur even if the inclination is not strictly determined. The information on the subject eyes E can be obtained by changing the reference values B1 in accordance with the importance of the determination of the inclination.

The eye information obtaining portions 21 configured as above are used in this embodiment. However, the eye information obtaining portions of the present disclosure are not limited to the ones in this embodiment. Other eye information obtaining portions may be used as long as the information on the subject eyes is obtained.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

What is claimed is:

1. An ophthalmologic apparatus comprising:
   eye information obtaining portions, each of the eye information obtaining portions corresponding to a respective subject eye of a subject and configured to obtain information on the respective subject eye;
   imaging portions, each of the imaging portions corresponding to a respective one of the eye information obtaining portions and configured to capture a subject eye image of the respective subject eye;
   a reference calculator configured to obtain a three-dimensional reference position in each of the subject eye images captured by each of the imaging portions;
   an inclination calculator configured to obtain inclination information indicating inclination of relative positions of the subject eyes from the obtained three-dimensional reference positions in the subject eye images; and
   a notification portion configured to notify the obtained inclination information when the inclination information exceeds a reference value while the eye information obtaining portions are obtaining the information on the subject eyes;
   wherein the notification portion comprises a plurality of reference values corresponding to operations of the eye information obtaining portions.

2. An ophthalmologic apparatus comprising:
   eye information obtaining portions, each of the eye information obtaining portions corresponding to a respective subject eye of a subject and configured to obtain information on the respective subject eye;
   imaging portions, each of the imaging portions corresponding to a respective one of the eye information obtaining portions and configured to capture a subject eye image of the respective subject eye;
   a reference calculator configured to obtain a three-dimensional reference position in each of the subject eye images captured by each of the imaging portions;
   an inclination calculator configured to obtain inclination information indicating inclination of relative positions of the subject eyes from the obtained three-dimensional reference positions in the subject eye images;
   a notification portion configured to notify the obtained inclination information; and
   reference projection portions, each of the reference projection portions corresponding to a respective subject eye and configured to project a light for forming a bright spot image to the respective subject eye,
   wherein the reference calculator is configured to obtain the three-dimensional position of the bright spot image in each of the subject eye images and set the obtained three-dimensional position as the three-dimensional reference position.

3. The ophthalmologic apparatus according to claim 2, wherein each of the imaging portions comprises two or more imaging devices each configured to capture an image of one of the subject eyes from a direction different from the other imaging devices, and
   wherein the reference calculator is configured to obtain the three-dimensional position of the bright spot image of each of the subject eyes based on the subject eye images captured by the two or more imaging devices.

4. The ophthalmologic apparatus according to claim 2, wherein the reference calculator is configured to obtain the three-dimensional position of the bright spot image of each of the subject eyes based on an aspect of the bright spot image in each of the subject eye images.

\* \* \* \* \*